United States Patent
Torgerson

(10) Patent No.: US 9,020,589 B2
(45) Date of Patent: Apr. 28, 2015

(54) ELECTRICAL STIMULATOR WITH VOLTAGE MODE EMULATION USING REGULATED CURRENT

(75) Inventor: Nathan A. Torgerson, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 943 days.

(21) Appl. No.: 12/768,309

(22) Filed: Apr. 27, 2010

(65) Prior Publication Data
US 2011/0264171 A1 Oct. 27, 2011

(51) Int. Cl.
*A61N 1/08* (2006.01)
*A61N 1/36* (2006.01)

(52) U.S. Cl.
CPC ............... *A61N 1/36* (2013.01); *A61N 1/3605* (2013.01); *A61N 1/36146* (2013.01)

(58) Field of Classification Search
USPC ...................................................... 607/45–46
See application file for complete search history.

(56) References Cited

U.S. PATENT DOCUMENTS

| | | | |
|---|---|---|---|
| 5,836,983 A | 11/1998 | Weijand et al. | |
| 5,895,416 A * | 4/1999 | Barreras et al. | 607/62 |
| 7,209,787 B2 * | 4/2007 | DiLorenzo | 607/45 |
| 7,317,948 B1 | 1/2008 | King et al. | |
| 7,387,603 B2 | 6/2008 | Gross et al. | |
| 7,389,147 B2 | 6/2008 | Wahlstrand et al. | |
| 7,519,428 B1 | 4/2009 | Palmer | |
| 7,571,007 B2 | 8/2009 | Erickson et al. | |
| 2003/0208244 A1 * | 11/2003 | Stein et al. | 607/48 |
| 2006/0247739 A1 | 11/2006 | Wahlstrand et al. | |
| 2006/0259079 A1 | 11/2006 | King | |
| 2007/0156206 A1 | 7/2007 | Wahlstrand et al. | |
| 2009/0149917 A1 | 6/2009 | Whitehurst et al. | |
| 2010/0023069 A1 | 1/2010 | Moffitt et al. | |
| 2010/0023070 A1 | 1/2010 | Moffitt et al. | |
| 2010/0106231 A1 | 4/2010 | Torgerson et al. | |

FOREIGN PATENT DOCUMENTS

| | | |
|---|---|---|
| EP | 0547482 A1 | 6/1993 |
| WO | WO 2009/076211 A1 | 6/2009 |
| WO | WO 2010/011721 A1 | 1/2010 |

OTHER PUBLICATIONS

U.S. Appl. No. 12/603,316, filed Oct. 21, 2009, Straka et al.
PCT International Search Report and Written Opinion dated May 27, 2011.

* cited by examiner

*Primary Examiner* — Brian T Gedeon
*Assistant Examiner* — Ankit Tejani
(74) *Attorney, Agent, or Firm* — Shumaker & Sieffert, P.A.

(57) ABSTRACT

Techniques are described for generating electrical stimulation current pulses for delivery of electrical stimulation therapy via a current-controlled system that emulates voltage pulses generated via a voltage-controlled system. In one example, a method includes receiving user input specifying a voltage level of electrical stimulation to be delivered by one or more of a plurality of electrodes implanted within the patient, selectively coupling the one or more electrodes to respective regulated current paths to deliver the electrical stimulation to the patient, selectively coupling at least another of the plurality of electrodes implanted within the patient to an unregulated current path to deliver the electrical stimulation to the patient, determining a regulated current for each respective regulated current path in order to produce the specified voltage level at the one or more electrodes selectively coupled to the respective regulated current paths, and delivering the determined regulated currents via the respective regulated current paths.

22 Claims, 9 Drawing Sheets

ELECTRICAL STIMULATOR WITH VOLTAGE MODE EMULATION USING REGULATED CURRENT

TECHNICAL FIELD

The disclosure relates to medical devices and, more particularly, to medical devices that deliver electrical stimulation therapy.

BACKGROUND

Medical devices may be used to treat a variety of medical conditions. Medical electrical stimulation devices, for example, may deliver electrical stimulation therapy to a patient via implanted electrodes. Electrical stimulation therapy may include stimulation of nerve, muscle, or brain tissue, or other tissue within a patient. An electrical stimulation device may be fully implanted within the patient. For example, an electrical stimulation device may include an implantable electrical stimulation generator and one or more implantable leads carrying electrodes. The electrical stimulation device may comprise a leadless stimulator. In some cases, implantable electrodes may be coupled to an external electrical stimulation generator via one or more percutaneous leads or fully implanted leads.

Medical electrical stimulators may be used to deliver electrical stimulation therapy to patients to relieve a variety of symptoms or conditions such as chronic pain, tremor, Parkinson's disease, depression, epilepsy, urinary or fecal incontinence, pelvic pain, sexual dysfunction, obesity, or gastroparesis. An electrical stimulator may be configured to deliver electrical stimulation therapy via leads that include electrodes implantable proximate to the spinal cord, pelvic nerves, gastrointestinal organs, peripheral nerves, or within the brain of a patient. Stimulation proximate the spinal cord and within the brain are often referred to as spinal cord stimulation (SCS) and deep brain stimulation (DBS), respectively.

A clinician selects values for a number of programmable stimulation parameters in order to define the electrical stimulation therapy to be delivered to a patient. For example, the clinician may select a current or voltage amplitude of the stimulation, and various characteristics of the stimulation waveform. In addition, the clinician may specify an electrode configuration used to deliver stimulation, including selected electrode combinations and electrode polarities. If the stimulation is delivered in the form of pulses, for example, the clinician may specify a pulse amplitude, pulse width and pulse rate. A set of parameter values may be referred to as a stimulation program. A program group may include multiple programs. Multiple programs in a program group may be delivered on a simultaneous, time-interleaved, or overlapping basis.

SUMMARY

In general, this disclosure describes techniques for delivering electrical stimulation therapy using controlled current pulses configured to emulate controlled voltage pulses. A controlled-current stimulation device may deliver electrical stimulation pulses having selected current levels. In a controlled-current stimulation device, the selected current level may remain substantially constant over a range of power and/or load conditions. A controlled-voltage stimulation device may deliver electrical stimulation pulses having selected voltage levels. In a controlled-voltage stimulation device, the selected voltage level may remain substantially constant over a range of power and/or load conditions. In some cases, a medical device may be configured as a controlled-voltage system or a controlled-current system, but may not include circuitry that produces both controlled-voltage and controlled-current pulses. However, it may be desirable to deliver controlled-voltage pulses or controlled-current pulses on a selective basis. Using various techniques described in this disclosure, a controlled-current stimulation device may generate controlled-current pulses that emulate controlled-voltage pulses that would be generated by a voltage-controlled stimulation device.

In one example, the disclosure is directed to a method for delivering electrical stimulation therapy. The method comprises receiving user input specifying a voltage level of electrical stimulation to be delivered by one or more of a plurality of electrodes implanted within the patient, selectively coupling the one or more electrodes to respective regulated current paths to deliver the electrical stimulation to the patient, selectively coupling at least another of the plurality of electrodes implanted within the patient to an unregulated current path to deliver the electrical stimulation to the patient, determining a regulated current for each respective regulated current path in order to produce the specified voltage level at the one or more electrodes selectively coupled to the respective regulated current paths, and delivering the determined regulated currents via the respective regulated current paths.

In another example, the disclosure is directed to a system for delivering electrical stimulation therapy. The device comprises a plurality of implantable electrodes, a user interface configured to receive user input from a user specifying a voltage level of electrical stimulation to be delivered by one or more of the plurality of electrodes, a stimulation controller, and a processor. The stimulation controller is configured to selectively couple the one or more electrodes to respective regulated current paths to deliver the electrical stimulation to the patient, and selectively couple at least another of the plurality of electrodes implanted within the patient to an unregulated current path to deliver the electrical stimulation to the patient. The processor is configured to determine a regulated current for each respective regulated current path in order to produce the specified voltage level at the one or more electrodes selectively coupled to the respective regulated current paths, and control delivery of the determined regulated currents via the respective regulated current paths.

In another example, the disclosure is directed to a computer-readable storage medium comprising instructions that, when executed by a processor, cause the processor to receive user input specifying a voltage level of electrical stimulation to be delivered by one or more of a plurality of electrodes implanted within the patient, selectively couple the one or more electrodes to respective regulated current paths to deliver the electrical stimulation to the patient, selectively couple at least another of the plurality of electrodes implanted within the patient to an unregulated current path to deliver the electrical stimulation to the patient, determine a regulated current for each respective regulated current path in order to produce the specified voltage level at the one or more electrodes selectively coupled to the respective regulated current paths, and control delivery of the determined regulated currents via the respective regulated current paths.

In another example, the disclosure is directed to a device for delivering electrical stimulation therapy, the device comprising means for receiving user input specifying a voltage level of electrical stimulation to be delivered by one or more of a plurality of electrodes implanted within the patient, means for selectively coupling the one or more electrodes to respective regulated current paths to deliver the electrical stimulation to the patient, means for selectively coupling at least another of the plurality of electrodes implanted within the patient to an unregulated current path to deliver the electrical stimulation to the patient, means for determining a regulated current for each respective regulated current path in order to produce the specified voltage level at the one or more electrodes selectively coupled to the respective regulated current paths, and means for delivering the determined regulated currents via the respective regulated current paths.

The details of one or more aspects of the disclosure are set forth in the accompanying drawings and the description below. Other features, objects, and advantages will be apparent from the description and drawings, and from the claims.

DETAILED DESCRIPTION

Figure 1:
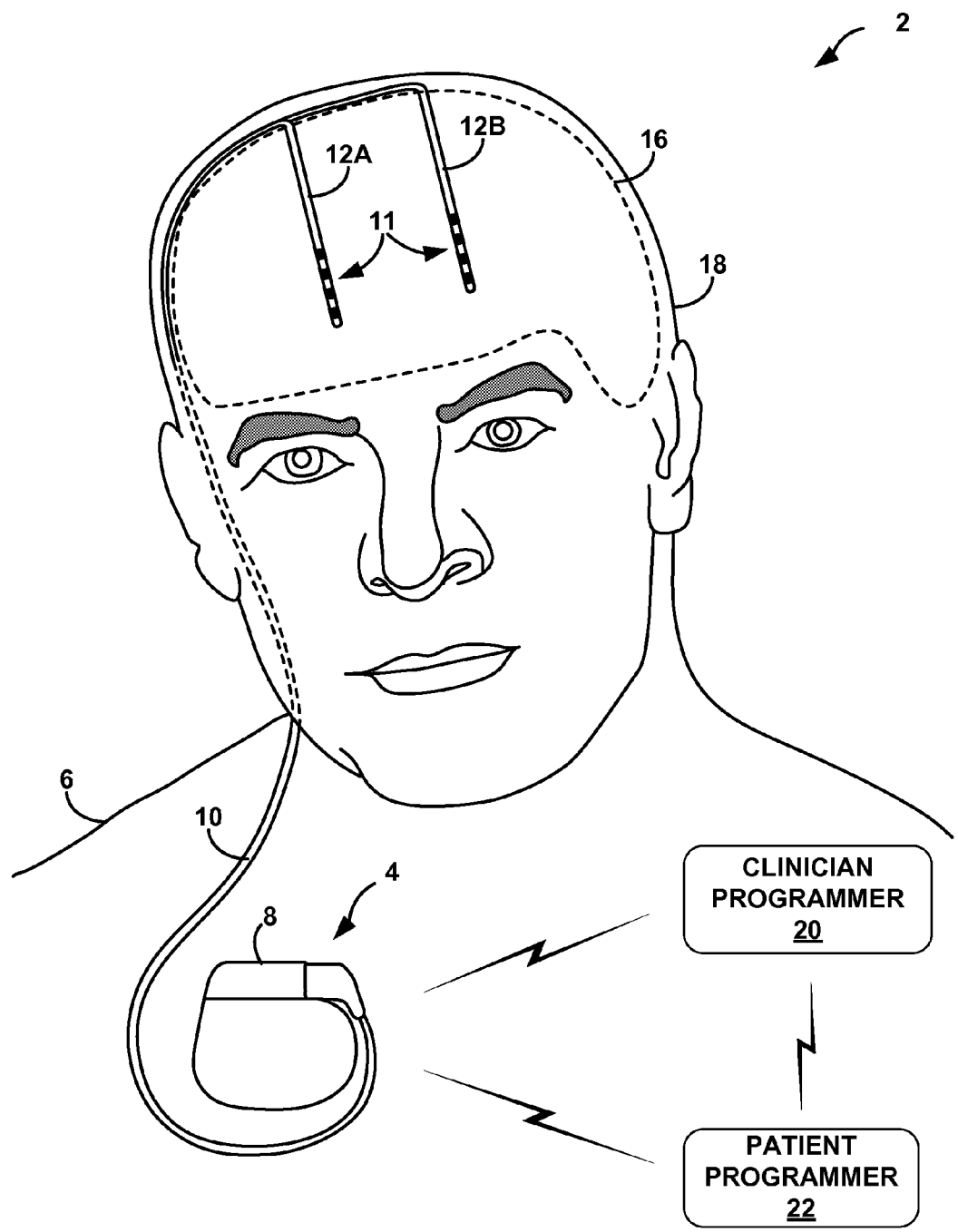
FIG. 1 is a conceptual diagram illustrating an example therapy system that includes an implantable stimulator coupled to a stimulation lead.

This disclosure describes techniques for generating electrical stimulation current pulses for delivery of electrical stimulation therapy via a controlled-current system that emulates voltage pulses generated via a controlled-voltage system. Medical devices, e.g., implantable medical devices and external medical devices, capable of delivery of electrical stimulation therapy are generally designed as either controlled-current systems, i.e., a current mode system, or controlled-voltage systems, i.e., a voltage mode system. A device configured as a controlled-current system, i.e., a current mode system, may generate regulated electrical stimulation current, e.g., pulses, via a current regulator to be delivered via one or more respective regulated electrodes. A device configured as a controlled-voltage system, i.e., a voltage mode system, may generate regulated electrical stimulation voltage, e.g., pulses, via a voltage regulator to be delivered via one or more respective regulated electrodes. Because such medical devices are often sized to be as small as possible in order to facilitate implantation, for example, it may be undesirable to include the different electronic circuitry capable of generating both controlled-current mode and controlled-voltage mode. Significant portions of the different electronic circuitry may be duplicative and, as such, may increase the size of the medical device. Hence, many medical devices capable of delivery of electrical stimulation therapy may only operate in either a voltage mode or a current mode.

Patients and physicians, however, may have a preference for a particular mode, i.e., current or voltage. For example, a given patient may prefer the feeling and the effects of the stimulation provided by an implanted medical device that operates in a voltage mode. On the other hand, another patient may prefer the effects of current mode stimulation. If a patient needs to have a medical device configured to operate in a particular mode replaced, the patient may prefer that it be replaced with a similar device. Such a device, however, may be unavailable or less preferred by the implanting physician. For example, the manufacturer of the currently implanted device may no longer manufacture the same or even a similar device that operates in voltage mode. Instead, the manufacturer may only produce devices that operate in current mode.

Using various techniques described in this disclosure, a device configured as a current mode system may emulate a device configured as a voltage mode system. As described in more detail below, using techniques of this disclosure, a user, e.g., clinician or patient, may specify a voltage level for an electrode carried by an implanted medical lead coupled to an implantable medical device. In this manner, the clinician or patient may program stimulation as if voltage mode stimulation is available, even though the stimulation device may actually be configured to deliver current mode stimulation. A regulated current, i.e., a controlled current, may be determined, e.g., by the implantable medical device or a programmer, for a regulated current path in order to produce the specified voltage level at the electrode. An unregulated electrode may be coupled to a reference voltage, e.g., a high reference voltage, low reference voltage, voltage regulator, or the like. The implantable medical device may then deliver the determined regulated current via the regulated current path. In this manner, the specified voltage is produced at the electrode by a controlled-current system. Hence, a voltage mode system is emulated by a current mode system.

FIG. 1 is a conceptual diagram illustrating an example system 2 that may be used to deliver stimulation therapy to patient 6. Patient 14 ordinarily, but not necessarily, will be a human. Generally, therapy system 2 includes implantable stimulator 4 that delivers an electrical stimulation to patient 6 via one or more implantable electrodes (not shown). The implantable electrodes may be deployed on one or more implantable medical leads, such as implantable medical lead 10. The electrical stimulation may be in the form of controlled-current pulses or substantially continuous waveforms. Various parameters of the pulses or waveforms may be defined by a stimulation program. The pulses or waveforms may be delivered substantially continuously or in bursts, segments, or patterns, and may be delivered alone or in combination with pulses or waveforms defined by one or more other stimulation programs. Although FIG. 1 shows a fully implantable stimulator 4, techniques described in this disclosure may be applied to external stimulators having electrodes deployed via percutaneously implantable leads. One or more of the electrodes may be located on a housing, i.e., "can," of the implantable stimulator 4. In addition, in some cases, implantable electrodes may be deployed on a leadless stimulator.

In the example illustrated in FIG. 1, implantable stimulator 4 is implanted within a subcutaneous pocket in a clavicle region of patient 6. Stimulator 4 generates programmable electrical stimulation, e.g., a current waveform or current pulses, and delivers the stimulation via an implantable medical lead 10 carrying an array of implantable stimulation electrodes 11. In some cases, multiple implantable leads may be provided. In the example of FIG. 1, a distal end of lead 10 is bifurcated and includes two lead segments 12A and 12B (collectively "lead segments 12"). Lead segments 12A and 12B each include a set of electrodes forming part of the array of electrodes 11. In various examples, lead segments 12A and 12B may each carry four, eight, or sixteen electrodes. In FIG. 1, each lead segment 12A, 12B carries four electrodes, configured as ring electrodes at different axial positions near the distal ends of the lead segments.

In some examples, lead 10 may also carry one or more sense electrodes to permit implantable stimulator 4 to sense electrical signals from patient 6. Some of the stimulation electrodes may be coupled to function as stimulation electrodes and sense electrodes on a selective basis. In other examples, implantable stimulator may be coupled to one or more leads which may or may not be bifurcated. In such examples, the leads may be coupled to implantable stimulator 4 via a common lead extension or via separate lead extensions. In addition, implantable stimulator 4 may, in some examples, include one or more electrodes on the housing in addition to the electrodes on lead segments 12.

A proximal end of lead 10 may be both electrically and mechanically coupled to header 8 on implantable stimulator 4 either directly or indirectly via a lead extension. Conductors in the lead body may electrically connect stimulation electrodes located on lead segments 12 to implantable stimulator 4. Lead 10 traverses from the implant site of implantable stimulator 4 along the neck of patient 6 to cranium 18 of patient 6 to access brain 16. Lead segments 12A and 12B are implanted within the right and left hemispheres, respectively, in order to deliver electrical stimulation to one more regions of brain 16, which may be selected based on the patient condition or disorder.

Implantable stimulator 4 may deliver, for example, deep brain stimulation (DBS) or cortical stimulation (CS) therapy to patient 6 via the electrodes carried by, i.e., located on, lead segments 12 to treat any of a variety of neurological disorders or diseases. Example neurological disorders may include depression, dementia, obsessive-compulsive disorder and movement disorders, such as Parkinson's disease, spasticity, epilepsy, and dystonia. DBS also may be useful for treating other patient conditions, such as migraines and obesity. However, the disclosure is not limited to the configuration of lead 10 shown in FIG. 1, or to the delivery of DBS or CS therapy.

Lead segments 12A, 12B may be implanted within a desired location of brain 16 through respective holes in cranium 18. Lead segments 12A, 12B may be placed at any location within brain 16 such that the electrodes located on lead segments 12A, 12B are capable of providing electrical stimulation to targeted tissue during treatment. Example locations for lead segments 12A, 12B within brain 26 may include the pedunculopontine nucleus (PPN), thalamus, basal ganglia structures (e.g., globus pallidus, substantia nigra, subthalmic nucleus), zona incerta, fiber tracts, lenticular fasciculus (and branches thereof), ansa lenticularis, and/or the Field of Forel (thalamic fasciculus). In the case of migraines, lead segments 12 may be implanted to provide stimulation to the visual cortex of brain 16 in order to reduce or eliminate migraine headaches afflicting patient 6. However, the target therapy delivery site may depend upon the patient condition or disorder being treated.

The electrodes of lead segments 12A, 12B are shown as ring electrodes. Ring electrodes are commonly used in DBS applications because they are simple to program and are capable of delivering an electrical field to any tissue adjacent to lead segments 12A, 12B. In other implementations, the electrodes of lead segments 12A, 12B may have different configurations. For example, the electrodes of lead segments 12A, 12B may have a complex electrode array geometry that is capable of producing shaped electrical fields. The complex electrode array geometry may include multiple electrodes (e.g., partial ring or segmented electrodes) around the perimeter of each lead segments 12A, 12B, rather than one ring electrode. In this manner, electrical stimulation may be directed in a specific direction from lead segments 12 to enhance therapy efficacy and reduce possible adverse side effects from stimulating a large volume of tissue. In alternative examples, lead segments 12 may have shapes other than elongated cylinders as shown in FIG. 1. For example, lead segments 12 may be paddle leads, spherical leads, bendable leads, or any other type of shape effective in treating patient 6.

Therapy system 2 also may include a clinician programmer 20 and/or a patient programmer 22. Clinician programmer 20 may be a handheld computing device that permits a clinician to program stimulation therapy for patient 6 via a user interface, e.g., using input keys and a display. For example, using clinician programmer 20, the clinician may specify stimulation parameters, i.e., create programs, for use in delivery of stimulation therapy. Clinician programmer 20 may support telemetry (e.g., radio frequency (RF) telemetry) with implantable stimulator 4 to download programs and, optionally, upload operational or physiological data stored by implantable stimulator 4. In this manner, the clinician may periodically interrogate implantable stimulator 4 to evaluate efficacy and, if necessary, modify the programs or create new programs. In some examples, clinician programmer 20 transmits programs to patient programmer 22 in addition to or instead of implantable stimulator 4.

Like clinician programmer 20, patient programmer 22 may be a handheld computing device. Patient programmer 22 may also include a display and input keys to allow patient 6 to interact with patient programmer 22 and implantable stimulator 4. In this manner, patient programmer 22 provides patient 6 with a user interface for control of the stimulation therapy delivered by implantable stimulator 4. For example, patient 6 may use patient programmer 22 to start, stop or adjust electrical stimulation therapy. In particular, patient programmer 22 may permit patient 6 to adjust stimulation parameters of a program such as duration, amplitude, e.g., voltage amplitude, pulse width and pulse rate. Patient 6 may also select a program, e.g., from among a plurality of stored programs, as the present program to control delivery of stimulation by implantable stimulator 4.

In some examples, implantable stimulator 4 delivers stimulation according to a group of programs at a given time. Each program of such a program group may include respective values for each of a plurality of therapy parameters, such as respective values for each of current amplitude, pulse width, pulse rate and electrode configuration. Implantable stimulator 4 may interleave pulses or other signals according to the different programs of a program group, e.g., cycle through the programs, to simultaneously treat different symptoms or different body regions, or provide a combined therapeutic effect. In such examples, clinician programmer 20 may be used to create programs, and assemble the programs into program groups. Patient programmer 22 may be used to adjust stimulation parameters of one or more programs of a program group, and select a program group, e.g., from among a plurality of stored program groups, as the current program group to control delivery of stimulation by implantable stimulator 4. In accordance with this disclosure, a user can use a controlled-voltage interface even though stimulator 4 is a controlled-current stimulator.

Implantable stimulator 4, clinician programmer 20, and patient programmer 22 may communicate via cables or a wireless communication, as shown in FIG. 1. Clinician programmer 20 and patient programmer 22 may, for example, communicate via wireless communication with implantable stimulator 4 using RF telemetry techniques known in the art. Clinician programmer 20 and patient programmer 22 also may communicate with each other using any of a variety of local wireless communication techniques, such as RF communication according to the 802.11 or Bluetooth specification sets, infrared communication, e.g., according to the IrDA standard, or other standard or proprietary telemetry protocols. Each of clinician programmer 20 and patient programmer 22 may include a transceiver to permit bi-directional communication with implantable stimulator 4.

System 2 delivers stimulation therapy to patient 6 in the form of controlled-current waveforms or controlled-current pulses. In other words, system 2 is configured to operate in current mode. A patient and/or clinician may, however, prefer the electrical stimulation provided by a system that operates in a voltage mode. In accordance with various techniques of this disclosure, system 2, although configured as a current mode system, may emulate a voltage mode system. Using clinician programmer 20 or patient programmer 22, for example, a user may specify a voltage level for one or more electrodes carried by an implanted medical lead coupled to an implantable medical device. A regulated current may be determined, e.g., by the implantable medical device or programmer, for a regulated current path in order to produce the specified voltage level at an electrode. An unregulated, reference electrode may sink or source unregulated current to reference voltage in order to counter-balance any unbalanced current produced by the regulated electrodes. The implantable medical device may then deliver the determined regulated current via the regulated current path. In this manner, the specified voltages are produced at one or more selected electrodes by a controlled-current system, i.e., current mode system, emulating a controlled-voltage system, i.e., voltage mode system.

In order to emulate a controlled-voltage system, implantable stimulator 4 regulates current that is sourced or sunk by one or more electrodes, referred to as regulated electrodes, and selectively couples one or more additional electrodes to an unregulated reference voltage, such as a high or low voltage supply rail, a common reference voltage, or a voltage regulator, thereby producing a specified voltage at one or more selected electrodes. Regulated electrodes may function as regulated anodes to source current or regulated cathodes to sink current. In order to produce a user specified voltage at a particular electrode, a current regulator generates regulated current to be delivered via a respective regulated electrode. The one or more electrodes coupled to the unregulated reference voltage may be referred to as "common electrodes" or "reference electrodes." An unregulated electrode may form a common anode or common cathode that sources or sinks, respectively, a sum of or difference between the currents produced by the regulated electrodes.

A source current may refer to a positive current that flows out of an electrode, e.g., from a regulated current source via a regulated current path to surrounding tissue, or from a reference voltage via an unregulated current path. A sink current may refer to a negative current that flows into an electrode, e.g. from surrounding tissue and is sunk by a regulated current sink via a regulated current path or by a reference voltage via an unregulated current path. Regulated source currents may sum to produce a greater overall source current. Regulated source and regulated sink currents may partially or entirely cancel one another. In the case of partial cancellation, the source and sink currents may produce a net difference in the form of a net source current or sink current. If provided, an unregulated current path can source or sink current approximately equal to this net difference.

An unregulated, reference electrode may sink or source unregulated current to counter-balance any unbalanced current produced by the regulated electrodes, such as a sum of regulated source currents, a sum of regulated sink currents, or a difference between regulated source and sink currents. In particular, the unregulated, reference electrode may counter-balance the unbalanced current by sinking or sourcing counter-balancing current to or from the reference voltage via an unregulated current path. The unregulated current path may be a direct connection provided by a simple switch.

An unregulated, reference electrode that is selectively coupled to sink current to a low reference voltage may be referred to as an unregulated cathode. An unregulated, reference electrode that is selectively coupled to source current from a high reference voltage may be referred to as an unregulated anode. The high or low reference voltage may be voltage-regulated but not current-regulated. For example, the high or low reference voltage may be generated via a voltage regulator. Consequently, the unregulated anode or cathode is coupled to the reference voltage via an unregulated current path. Typically, controlled-current stimulation therapies regulate current at each stimulation electrode so that there is a balance in charge between the stimulation electrodes. However, the use of regulated current paths for all electrodes may cause increased power consumption, which is generally undesirable in medical devices, such as implantable medical devices that are typically powered by limited battery resources.

Using various techniques of this disclosure, stimulator 4 may emulate a voltage mode system by using electrodes configured as regulated current sources or sinks, in combination with one or more electrodes coupled to reference voltage via an unregulated current path. Stimulator 4 may reduce the power consumption overhead otherwise associated with control and feedback circuitry in a regulated current source or sink by coupling one or more electrodes to a reference voltage, via an unregulated current path. Implantable stimulator 4 may be configured to provide selective control of electrodes so that each electrode may be programmed to provide a regulated current source, a regulated current sink, an unregulated current source, or an unregulated current sink.

For example, stimulator 4 may use a common anode and individual cathode current control capability in order to emulate a voltage mode system. That is, in order to produce a specified voltage at one or more selected cathodes, one or more anodes may be programmed to a common reference voltage and stimulator 4 (or stimulator 34) may control the individual cathode current that is required to be sunk by one or more current regulators coupled to the selected cathodes. For example, in order to produce a specified voltage of 4 volts (V) at a first electrode (cathode), stimulator 4 may couple a second electrode (anode) to a high reference voltage and then determine a current required to be sunk by a current regulator coupled to the first electrode (cathode). As the load at the electrode changes, the voltage at the electrode changes. In some example implementations, based on a measured voltage at the electrode, stimulator 4 may adjust the amount of current sunk by the first electrode (cathode) in order to maintain the specified voltage of 4V at the first electrode.

As another example, stimulator 4 may use a common cathode and individual anode current control capability in order to emulate a voltage mode system. In such an example implementation, in order to produce a specified voltage at one or more selected anodes, one or more cathodes may be programmed to a common reference voltage and stimulator 4 (or stimulator 34) may control the individual anode current that is required to be sourced by one or more current regulators coupled to the selected anodes. For example, in order to produce a specified voltage of 4V at a first electrode (anode), stimulator 4 may couple a second electrode (cathode) to a low reference voltage and then determine a current required to be source by a current regulator coupled to the first electrode (anode). As the load at the electrode changes, the voltage at the electrode changes. In some example implementations, based on a measured voltage at the electrode, stimulator 4 may adjust the amount of current sourced by the first electrode (anode) in order to maintain the specified voltage of 4V at the first electrode.

Utilizing a common anode or common cathode in order to emulate a voltage mode system may increase battery life by reducing the number of electrodes that are required to be current regulated. Increased battery life may be achieved because current regulator circuitry can be turned OFF for electrodes operating as unregulated current sources or sinks. In this manner, the power consumption overhead associated with at least some of the regulated current sources or sinks can be reduced or eliminated.

In addition, coupling one or more electrodes to a reference voltage or voltage regulator, and thus producing a common electrode configuration, may reduce the complexity of programming by eliminating the need to program controlled current or voltage levels for the common electrodes. Unlike a regulated electrode coupled to a regulated current path, the unregulated electrode is coupled to a reference voltage via an unregulated current path and, in general, will source or sink whatever amount of current is needed. In other words, for the unregulated electrode, there is no need to program a particular current level for a regulated current sink (either directly, as in current mode systems, or indirectly, as in current mode systems that emulate voltage mode systems), as would be required for a regulated electrode. Instead, the unregulated electrode is passive and simply directs current to and from a reference voltage depending on whether a positive, source current or a negative, sink current is need to counterbalance the regulated current. Accordingly, the use of one or more unregulated electrodes, i.e., unregulated anodes or unregulated cathodes, in an electrode configuration can contribute to reduction in programming complexity.

For a given electrode configuration, stimulator 4 may be programmed to emulate a voltage mode system by configuring one or more electrodes to operate as either regulated current sources or regulated current sinks, while one or more other electrodes are configured to operate as either unregulated current sources or unregulated current sinks in order to produce user-specified voltages at one or more selected electrodes. The unregulated reference electrode may be selected to be either one or more cathodes that sink current to a reference voltage, or one or more anodes that source current from a reference voltage, depending on the programming of the regulated electrodes. The regulated and unregulated electrodes form an electrode configuration.

The electrode configuration may be programmed using a programmer, such as clinician programmer 20 or patient programmer 22. In programming the electrode configuration to emulate a voltage mode system, the user, e.g., physician, technician, or patient, may specify a particular electrode configuration by, for example, selecting particular electrodes and assigning desired voltages to the selected electrodes, as well as other parameters for a stimulation program. Stimulator 4, however, operates on limited battery resources and, as such, has headroom restrictions that affect the practical operation of the system. It is generally assumed for the examples provided throughout this description that there is sufficient headroom to support the specified electrode configuration. That is, it is generally assumed that the voltage rails are sufficiently separated to support the specified current paths, and that the unregulated cathodes and/or anodes do not pull the common mode of the system too far to the top or bottom rail such that the regulated current paths cannot support the programmed current.

Figure 2:
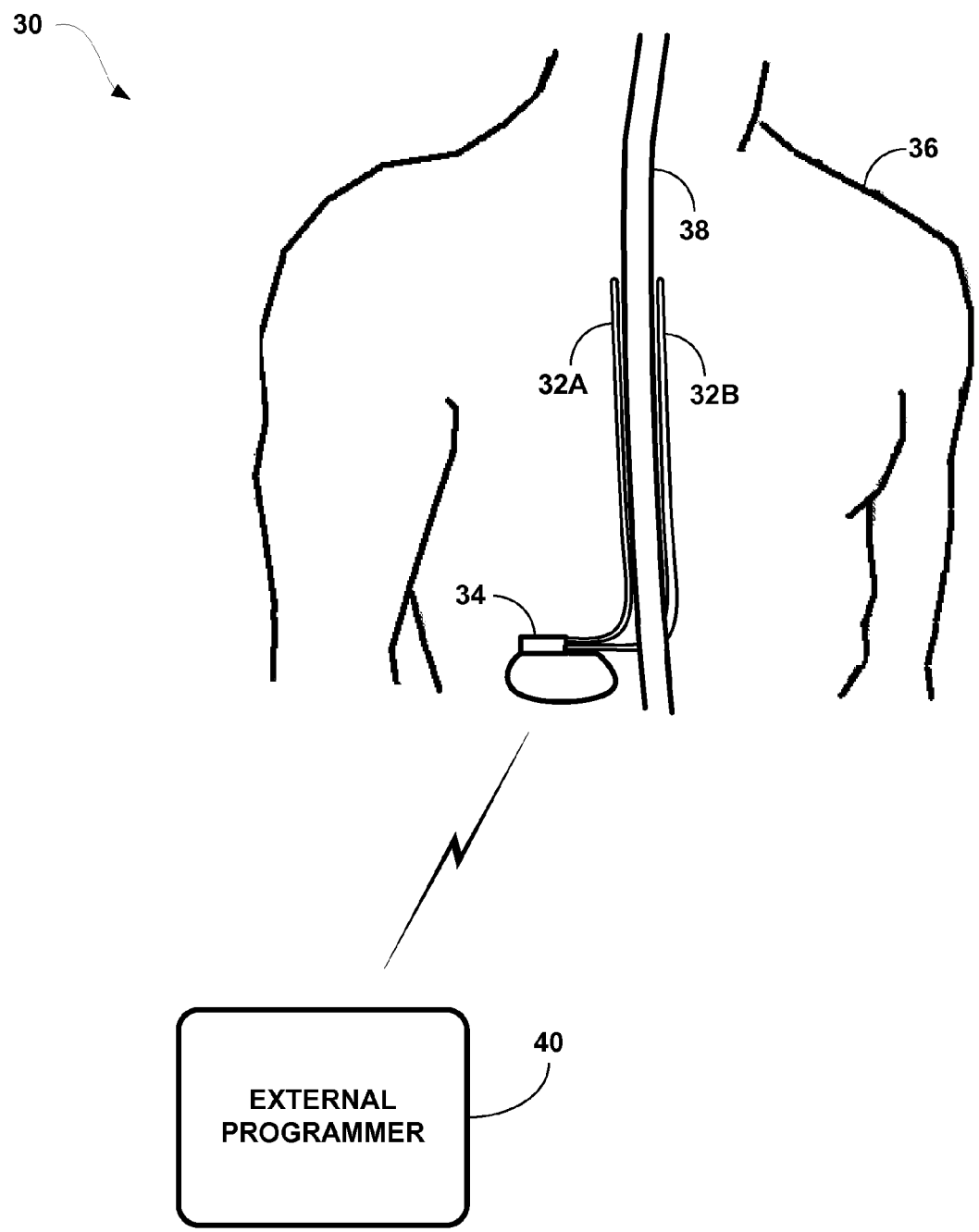
FIG. 2 is a conceptual diagram illustrating another example therapy system that includes an implantable stimulator coupled to a stimulation lead.

FIG. 2 is a conceptual diagram illustrating system 30 that delivers stimulation therapy to spinal cord 38 of patient 36. Hence, like FIG. 1, FIG. 2 represents another example of an electrical stimulation system that may support techniques described in this disclosure. Other electrical stimulation systems may be configured to deliver electrical stimulation to gastrointestinal organs, pelvic nerves or muscle, peripheral nerves, or other stimulation sites. In the example of FIG. 2, system 30 delivers stimulation therapy from implantable stimulator 34 to spinal cord 38 via one or more electrodes (not shown) carried by, i.e., located on, implantable medical leads 32A and 32B (collectively "leads 32"). System 30 and, more particularly, implantable stimulator 34 may operate in a manner similar to implantable stimulator 4 (FIG. 1). That is, implantable stimulator 34 may emulate a voltage mode system by delivering controlled-current stimulation pulses or waveforms to patient 36 via one or more regulated, stimulation electrodes and one or more unregulated, reference electrodes in order to produce user-specified voltages at the one or more regulated electrodes. In typical implementations, two or more regulated electrodes may be used in conjunction with one or more unregulated electrodes.

In the example of FIG. 2, the distal ends of leads 32 carry electrodes that are placed adjacent to the target tissue of spinal cord 38. The proximal ends of leads 32 may be both electrically and mechanically coupled to implantable stimulator 4 either directly or indirectly via a lead extension and header. Alternatively, in some examples, leads 32 may be implanted and coupled to an external stimulator, e.g., through a percutaneous port. In additional example implementations, stimulator 34 may be a leadless stimulator with one or more arrays of electrodes arranged on a housing of the stimulator rather than leads that extend from the housing. Application of certain techniques will be described herein with respect to implantable stimulator 34 and implantable leads 32 having ring electrodes for purposes of illustration. However, other types of electrodes may be used.

Stimulator 34 may be implanted in patient 36 at a location minimally noticeable to the patient. Alternatively, stimulator 34 may be external with percutaneously implanted leads. For SCS, stimulator 34 may be located in the lower abdomen, lower back, or other location to secure the stimulator. Leads 32 are tunneled from stimulator 34 through tissue to reach the target tissue adjacent to spinal cord 38 for stimulation delivery. At the distal ends of leads 32 are one or more electrodes (not shown) that transfer the stimulation pulses from the lead to the tissue. The electrodes may be electrode pads on a paddle lead, circular (i.e., ring) electrodes surrounding the body of leads 32, conformable electrodes, cuff electrodes, segmented electrodes, or any other type of electrodes capable of forming unipolar, bipolar or multi-polar electrode configurations.

Implantable stimulator 34 delivers stimulation to spinal cord 38 to reduce the amount of pain perceived by patient 36. As mentioned above, however, the stimulator may be used with a variety of different therapies, such as peripheral nerve stimulation (PNS), peripheral nerve field stimulation (PNFS), deep brain stimulation (DBS), cortical stimulation (CS), pelvic floor stimulation, gastric stimulation, and the like. The stimulation delivered by implantable stimulator 34 may take the form of stimulation pulses or continuous stimulation waveforms, and may be characterized by controlled current levels, as well as programmed pulse widths and pulse rates in the case of stimulation current pulses. Stimulation may be delivered via selected combinations of electrodes located on one or both of leads 32. Stimulation of spinal cord 38 may, for example, prevent pain signals from traveling through the spinal cord and to the brain of the patient. Patient 34 perceives the interruption of pain signals as a reduction in pain and, therefore, efficacious therapy.

With reference to FIG. 2, a user, such as a clinician or patient 36, may interact with a user interface of external programmer 40 to program stimulator 34. Programming of stimulator 34 may refer generally to the generation and transfer of commands, programs, or other information to control the operation of the stimulator. For example, programmer 40 may transmit programs, parameter adjustments, program selections, group selections, or other information to control the operation of stimulator 34, e.g., by wireless telemetry. As one example, programmer 40 may transmit parameter adjustments to support parameter-directed shifting of electrode combinations used to deliver stimulation according to a selected program.

In some cases, external programmer 40 may be characterized as a physician or clinician programmer, such as clinician programmer 20 (FIG. 1), if it is primarily intended for use by a physician or clinician. In other cases, external programmer 40 may be characterized as a patient programmer, such as patient programmer 22 (FIG. 1), if it is primarily intended for use by a patient. In general, a physician or clinician programmer may support selection and generation of programs by a clinician for use by stimulator 34, whereas a patient programmer may support adjustment and selection of such programs by a patient during ordinary use.

Whether programmer 40 is configured for clinician or patient use, programmer 40 may communicate to implantable stimulator 4 or any other computing device via wireless communication. Programmer 40, for example, may communicate via wireless communication with implantable stimulator 4 using radio frequency (RF) telemetry techniques known in the art. Programmer 40 may also communicate with another programmer or computing device via a wired or wireless connection using any of a variety of local wireless communication techniques, such as RF communication according to the 802.11 or Bluetooth specification sets, infrared communication according to the IRDA specification set, or other standard or proprietary telemetry protocols. Programmer 40 may also communicate with another programming or computing device via exchange of removable media, such as magnetic or optical disks, or memory cards or sticks. Further, programmer 40 may communicate with implantable stimulator 4 and other programming devices via remote telemetry techniques known in the art, communicating via a local area network (LAN), wide area network (WAN), public switched telephone network (PSTN), or cellular telephone network, for example.

Figure 3:
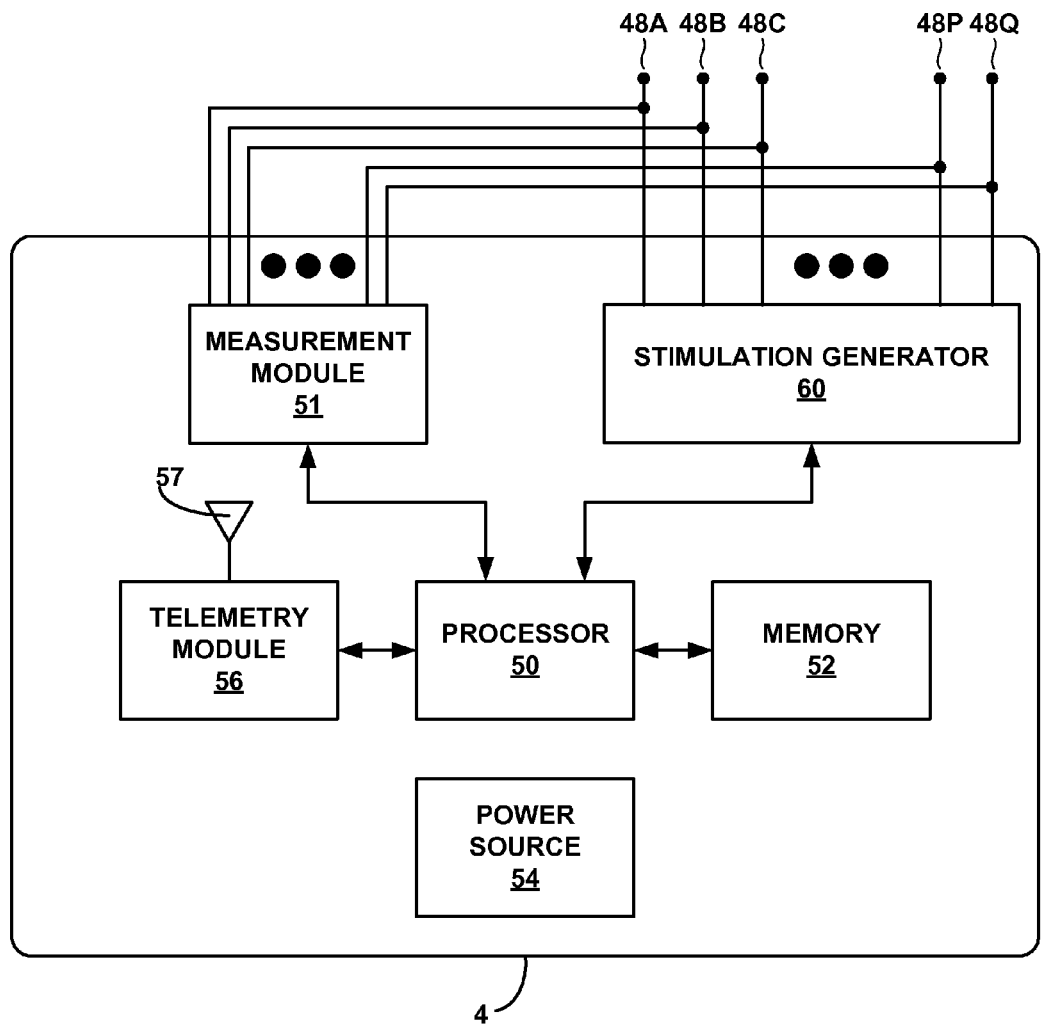
FIG. 3 is a block diagram illustrating various example components of an implantable electrical stimulator.

FIG. 3 is a block diagram illustrating various components of an example implantable stimulator 4. Although the components shown in FIG. 3 are described in reference to implantable stimulator 4, the components may also be included within implantable stimulator 34 shown in FIG. 2 and used within system 30. In the example of FIG. 3, implantable stimulator 4 includes processor 50, measurement module 51, memory 52, power source 54, telemetry module 56, antenna 57, and stimulation generator 60. Implantable stimulator 4 is also shown in FIG. 3 coupled to electrodes 48A-Q (collectively "electrodes 48"). Electrodes 48A-48P are implantable and may be deployed on one or more implantable leads. With respect to FIG. 1, lead segments 12A and 12B may carry electrodes 48A-H and electrodes 48I-P, respectively. In some cases, one or more additional electrodes may be located on or within the housing of implantable stimulator 4, e.g., to provide a common or ground electrode. With respect to FIG. 2, leads 32A and 32B may carry electrodes 48A-H and electrodes 48I-P, respectively. In the examples of FIGS. 1 and 2, a lead or lead segment carries eight electrodes to provide an 2×8 electrode configuration (two leads with 8 electrodes each), providing a total of sixteen different electrodes. The leads may be detachable from a housing associated with implantable stimulator 4, or be fixed to such a housing.

In other examples, different electrode configurations comprising a single lead, two leads, three leads, or more may be provided. In addition, electrode counts on leads may vary and may be the same or different from a lead to lead. Examples of other configurations include one lead with eight electrodes (1×8), two leads with four electrodes each (2×4), three leads with four electrodes each (3×4), three leads with eight electrodes each (3×8), three leads with four, eight, and four electrodes, respectively (4-8-4), or other configurations. Different electrodes are selected to form electrode combinations. Polarities are assigned to the selected electrodes to form electrode configurations.

Electrode 48Q represents one or more electrodes that may be carried on a housing, i.e., can, of implantable stimulator 4. Electrode 48Q may be configured as a regulated or unregulated electrode for use in an electrode configuration with selected regulated and/or unregulated electrodes among electrodes 48A-48Q, which may be located by one or more leads, as described above. As further alternatives, in some examples, electrodes 48A-48Q may be formed together on an integrated, leadless implantable stimulator 4. For example, electrodes 48A-48Q may be formed together on a housing that carries the electrodes and houses the components of implantable stimulator 4, such as stimulation generator 60, processor 50, memory 52, telemetry module 56, and power source 54.

The housing that carries electrodes 48A-48Q may be a unitary housing or a housing that combines submodules in a fixed or movable relationship with respect to one another. For example, stimulation generator housing submodule may be coupled to an electrode housing submodule. In each case, the electrodes 48A-48Q are provided on the housing or housing submodule instead of on an elongated lead or leads. Two or more regulated electrodes located on the housing may be combined with one or more unregulated electrodes located on the housing to form various electrode configurations as described in this disclosure.

Selected electrodes may be configured via switches or adaptable current regulators to provide regulated or unregulated current paths within the electrode configuration on a selection basis. The regulated or unregulated current paths may be source or sink paths. In this manner, regulated, bi-directional constant current sources can be used in conjunction with one or more reference electrodes. The current regulators control the amount of current being delivered or received via respective regulated electrodes. The unregulated, reference electrode can be used to balance any potential unbalanced charge that may be delivered between the regulated current sources and the regulated current sinks during delivery of a stimulation waveform or pulses.

Memory 52 may store instructions for execution by processor 50, stimulation therapy data, sensor data, and/or other information regarding therapy for patient 6. Processor 50 may control stimulation generator 60 to deliver stimulation according to a selected one or more of a plurality of programs or program groups stored in memory 52. Memory 52 may include any electronic data storage media, such as random access memory (RAM), read-only memory (ROM), electronically-erasable programmable ROM (EEPROM), flash memory, or the like. Memory 52 may store program instructions that, when executed by processor 50, cause the processor to perform various functions ascribed to processor 50 and implantable stimulator 4 in this disclosure.

In accordance with techniques of this disclosure, a user may program electrical stimulation parameters, such as pulse parameters, in terms of voltage amplitude, rather than current amplitude. For example, a patient may use patient programmer 22 to specify the voltage amplitude that the user desires stimulator 4, for example, to produce at particular electrodes. Programmer 22 then transmits these parameters to stimulator 4 via telemetry module 56. In response, processor 50 controls stimulation generator 60 to deliver a pulse and measurement module 51 to measure the voltage of the pulse as it ramps upward towards the user-specified voltage amplitude. Processor 50 then controls stimulation generator 60 to stop increasing the voltage of the pulse once the user-specified, or target, voltage is delivered for each programmed voltage. If decreasing, processor 50 controls stimulation generator 60 to deliver a pulse and measurement module 51 to measure the voltage of the pulse as it ramps downward towards the user-specified voltage amplitude. Processor 50 then controls stimulation generator 60 to stop decreasing the voltage of the pulse once the user-specified, or target, voltage is delivered for each programmed voltage. In some examples, measurement module 51 may sample in the middle of the pulse in order to provide an average impedance over the duration of the pulse. In this manner, the total charge delivered for the controlled-current pulse is approximately the same as what would have been delivered by an equivalent controlled-voltage pulse.

In another example, a patient may use patient programmer 22 to specify the voltage amplitude that the user desires stimulator 4, for example, to produce at particular electrodes. Programmer 22 then transmits these parameters to stimulator 4 via telemetry module 56. Processor 50 controls measurement module 51 to measure the impedance between the common anode (or common cathode) and each cathode (or anode) used for the program and then program a current to match the desired voltage. Measurement module 51 may sample in the middle of the pulse in order to provide an average impedance over the duration of the pulse. In this manner, the total charge delivered for the controlled-current pulse is approximately the same as what would have been delivered by an equivalent controlled-voltage pulse. Using an average impedance allows the use of Ohm's Law (V=I*Z) to compute the programmed current necessary for a controlled-current pulse.

In another example, patient programmer 22 may command stimulator 4 and, in particular, measurement module 51 to take impedance measurements. Programmer 22 may retrieve the impedance measurements from stimulator 4 via telemetry and then processor 53 of programmer 22 may convert, using Ohm's Law, the user-specified voltage to the proper current amplitude setting for an equivalent controlled-current pulse.

Processor 50 may include one or more microprocessors, digital signal processors (DSPs), application-specific integrated circuits (ASICs), field-programmable gate arrays (FPGAs), or other digital logic circuitry. Processor 50 controls operation of implantable stimulator 4, e.g., controls stimulation generator 60 to deliver stimulation therapy according to a selected program or group of programs retrieved from memory 52. For example, processor 50 may control stimulation generator 60 to deliver electrical signals, e.g., as stimulation pulses or continuous waveforms, with current amplitudes, pulse widths (if applicable), and rates specified by one or more stimulation programs. Processor 50 may also control stimulation generator 60 to selectively deliver the stimulation via subsets of electrodes 58, also referred to as electrode combinations, and with polarities specified by one or more programs.

Upon selection of a particular program group, processor 50 may control stimulation generator 60 to deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate, if applicable. For a continuous waveform, parameters may include amplitude and frequency. In addition, each program may specify a particular electrode combination for delivery of stimulation, and an electrode configuration in terms of the polarities and regulated/unregulated status of the electrodes. Again, the electrode combination may specify particular electrodes in a single array or multiple arrays, and on a single lead or among multiple leads.

Stimulation generator 60 is electrically coupled to electrodes 48A-P via conductors of the respective lead, such as lead segments 12 in FIG. 1 or leads 32 in FIG. 2, in implementations in which electrodes 48A-P are carried by, located on, leads. If one or more housing ("can") electrodes 48Q are provided, stimulation generator 60 may be electrically coupled to such an electrode via an electrical conductor disposed within the housing of implantable stimulator 4 (FIG. 1) or implantable stimulator 34 (FIG. 3). A can electrode 48Q may be configured as a regulated or unregulated electrode to form an electrode configuration in conjunction with two or more of electrodes 48P-48Q, which may be located on leads or on the housing of stimulator 4.

Stimulation generator 60 may include stimulation generation circuitry to generate stimulation pulses or waveforms and circuitry for switching stimulation across different electrode combinations, e.g., in response to control by processor 50. Stimulation generator 60 produces an electrical stimulation signal in accordance with a program based on control signals from processor 50.

For example, stimulation generator 60 may include a charging circuit that selectively applies energy from power source 54 to a capacitor module for generation and delivery of a supply voltage for generation of stimulation signal. In addition to capacitors, the capacitor module may include switches. In this manner, the capacitor module may be configurable, e.g., based on signals from processor 50, to store a desired voltage for delivery of stimulation at a voltage or current amplitude specified by a program. For delivery of stimulation pulses, switches within the capacitor module may control the widths of the pulses based on signals from processor 50.

Stimulation generator 60 may be capable of delivering stimulation using two or more of electrodes 48A-Q as stimulation electrodes and a different one or more of electrodes 48A-Q as reference electrodes. Accordingly, stimulation generator 60 may include stimulation circuitry such as bi-directional, regulated current sources for each of electrodes 48A-Q. Again, a bi-directional current source may refer to a regulated current source or sink on an interchangeable basis. A regulated current source or sink may generate regulated currents using a supply voltage provided by a capacitor module as described above. In one example, stimulation generator 60 includes an array of regulated bi-directional current sources and an array of switches. Electrodes 48A-Q may be selectively coupled to a reference voltage via the switches.

Figure 6:
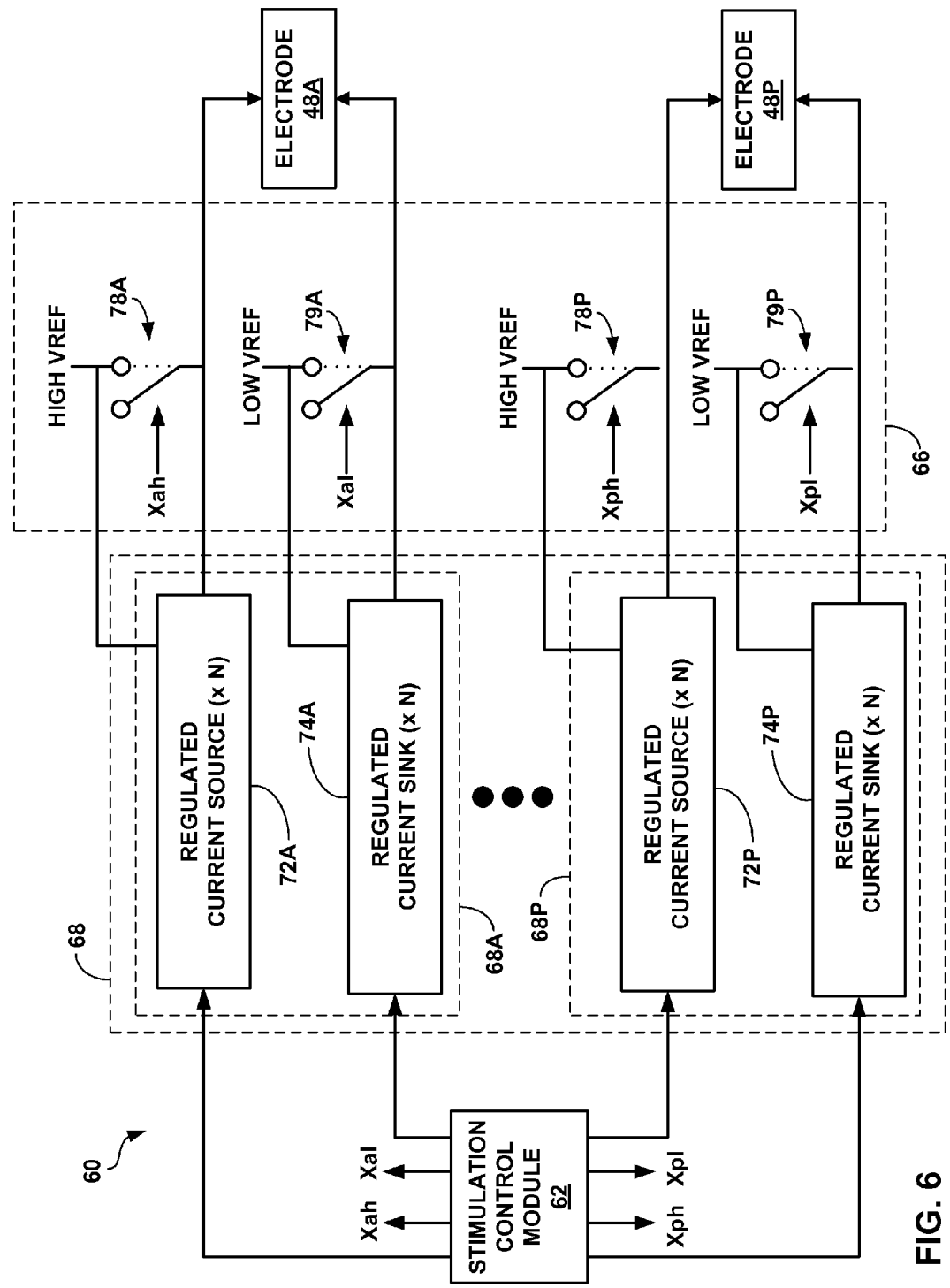
FIG. 6 is a block diagram illustrating the example stimulation generator of FIG. 5 in greater detail.

The reference voltage may be a high reference voltage for unregulated anodic operation or a low reference voltage for unregulated cathodic operation, each of which may be provided by a capacitor module as described above. Again, the capacitor module may be configurable, based on signals from processor 50, to store a desired voltage for use by a regulated current source or sink to deliver of current-based stimulation pulses as specified by a program. When an electrode is used as a regulated electrode, an associated regulated current source or sink may be activated. The current source or sink may be directly coupled to the electrode with or without an intervening switch. If the current source or sink is not turned ON, the electrode will not be active unless it is coupled by a switch to a high or low reference voltage for unregulated operation. An example configuration for this example is shown in FIG. 6.

In another example, stimulation generator 60 includes adaptable stimulation circuitry for each of electrodes 48 A-Q, in which case separate switches to form unregulated electrodes may be omitted in some implementations. The adaptable stimulation circuitry may include adaptable regulated current sources that, in effect, may operate as either a regulated current source or an unregulated switch that couples an electrode to a reference voltage.

In accordance with techniques of this disclosure, electrical measurement module 51 monitors signals from one or more of electrodes 48A-48Q in order to determine the regulated current needed to produce the voltage level specified by the user. Again, stimulation generator 60 is configured to produce electrical stimulation in the form of controlled-current pulses or substantially continuous waveforms. Electrical measurement module 51 is used to determine a regulated current for a respective regulated current path in order to produce a specified voltage level at the one or more electrodes selectively coupled to the respective regulated current path. Measurement module 51 measures voltages from one or more of electrodes 48A-48Q thereby allowing processor 50 to determine the current required to be sourced or sunk by the current regulators of stimulation generator 60 in order to produce the voltage levels specified by the user. Measurement module 51 may include a switch module to select specific electrodes to monitor.

In one example, a user may select a program stored in memory 52 that delivers electrical stimulation therapy using three electrodes, namely electrodes 48A and 48B, with electrode 48C configured as a reference, or common, electrode. Assume for this example that electrodes 48A and 48B are configured as cathodes and electrode 48C is configured as a common anode, i.e., electrode 48C is coupled to a high voltage reference. As such, electrodes 48A and 48B sink current and electrode 48C sources current. Using techniques mentioned above and described in more detail below with respect to FIG. 6, stimulation generator couples electrodes 48A and 48B to regulated current sinks in order to sink the amount of current required to produce the user specified voltage levels at electrodes 48A and 48B, and couples electrode 48C to a reference voltage in order to source the same amount current to produce a net charge delivery to the patient of zero.

Because the user may be more comfortable thinking of stimulation therapy in terms of voltage rather than current, the program may store voltage, rather than current, settings for electrodes 48A and 48B. Or, the program may store current settings, but the programmer, e.g., programmer 20, 22, or 40, may present voltage settings to the user. By way of specific example, the user may have created a program such that electrode 48A has a specified voltage of 4V and electrode 48B has a specified voltage of 5V. However, as indicated above, stimulation generator is a current mode system. Measurement module 51 of stimulator 4 monitors signals at electrodes 48A-48C in order for processor 50 (or processor 53 of FIG. 4) to determine the regulated current required to produce 4V at electrode 48A and 5V at electrode 48B.

Numerous techniques may be used by stimulator 4 and measurement module 51 to determine the regulated current required to produce the desired voltages at electrodes 48A and 48B. For instance, an impedance may be determined between common electrode 48C and each of the selected electrodes, e.g., electrodes 48A, 48B. Using the current regulators coupled to a selected electrode, e.g., electrode 48A, stimulation generator 60 applies a small test current and measurement module 51 measures the voltage developed between common electrode 48C and electrode 48A. By solving Ohm's Law ($V=I*Z$), processor 50 may determine impedance Z between the two electrodes from the known test current I delivered by stimulation generator 60 and the voltage V measured by measurement module 51. Then, using the determined impedance Z and Ohm's Law, processor 50 may determine, e.g., calculate, the current I that the current regulator coupled to electrode 48A must sink in order to produce the specified voltage of 4V at electrode 48A.

Measurement module 51 and processor 50 may similarly determine the current required to produce a voltage of 5V at electrode 48B. Using the current regulators coupled to the selected electrode, e.g., electrode 48B, a small test current is applied and measurement module 51 measures the voltage developed between common electrode 48C and electrode 48B. The test current may be a subthreshold pulse, e.g., with an amplitude between about 0.1 mA and about 0.4 mA and with a pulse width of about 80 microseconds. By solving Ohm's law ($V=I*Z$), processor 50 may determine impedance Z between the two electrodes from the known test current I delivered by stimulation generator 60 and voltage V measured by measurement module 51. Then, using the determined impedance Z and Ohm's Law, processor 50 may determine, e.g., calculate, the current I that the current regulator coupled to electrode 48B must sink in order to produce the specified voltage of 5V at electrode 48B. In this manner, stimulator 4, configured to operate in a current mode, may emulate a voltage mode system. It should be noted that, in some examples, stimulator 4 may actively deliver stimulation to the patient while measurement module 51 is monitoring signals at one or more of electrodes 48A-48Q and while processor 50 is performing any required calculations. For instance, a sampling circuit that measures the voltage being delivered during the controlled current therapy pulse may used.

The specific example above described coupling electrodes 48A and 48B to regulated sinks and coupling electrode 48C to an unregulated current path, e.g., high voltage reference or voltage regulator to produce a common anode. However, the techniques of this disclosure are not so limited. Rather, in some example implementations, stimulator 4 may couple electrodes 48A and 48B, for example, to regulated sources and couple electrode 48C to an unregulated current path, e.g., low voltage reference or voltage regulator, to produce a common cathode.

In addition, the specific example above described using a single electrode, namely electrode 48C, as a common electrode. In some examples, it may be desirable to use more than one electrode as a common electrode. For instance, electrodes 48D and 48E may also be coupled to an unregulated current path and act as common electrodes. Adding more common electrodes, e.g., anodes, may improve the efficiency of stimulator 4 because configuring additional common electrodes may reduce the impedance for the regulated electrodes, e.g., cathodes, to deliver their current, thereby decreasing the voltage required.

Another technique that may be used by stimulator 4 and measurement module 51 to determine the regulated current required to produce the desired voltages at electrodes 48A and 48B involves measurement module 51 taking a voltage measurement at the selected electrode and stimulation generator 60 adjusting the regulated current as necessary to produce the desired voltage level at the selected electrode. Continuing the example above, the user-selected stimulation program specifies a voltage at electrode 48A of 4V and a voltage at electrode 48B of 5V. A current regulator delivers electrical current via a respective regulated current path to electrodes 48A and 48B. Measurement module 51 measures the voltages at electrode 48A and at electrode 48B, and processor 50 adjusts the current sunk by current regulators coupled to electrodes 48A and 48B in response to the measured voltage in order to produce the specified voltages.

For instance, measurement module 51 may measure 3V at electrode 48A and 6V at electrode 48B. In response, processor 50 controls the current regulator coupled to electrode 48A to increase the amount of regulated current that the current regulator is sinking to increase the voltage at electrode 48A from 3V to 4V. As the current regulator increases the amount of current it is sinking, measurement module 51 measures the voltage at electrode 48A. Once measurement module 51 senses a voltage of 4V at electrode 48A, processor 50 controls the current regulator coupled to electrode 48A to continue to sink that particular amount of current, thereby maintaining 4V at electrode 48A (assuming that the load impedance does not change).

By way of specific example, processor 50 may control the current regulator coupled to electrode 48A to increase the current sunk from 2.0 milliamps (mA) to 2.1 mA in order to increase the voltage at electrode 48A from 3.8V to 4.0V. Of course, step sizes greater than 0.1 mA or less than 0.1 mA may be desirable. Then, processor may control measurement module 51 to measure the voltage at electrode 48A. If the voltage at electrode 48A is 4V, processor 50 does not increase the current sunk by the current regulator coupled to electrode 48A. However, if the voltage is still less than 4V, processor 50 controls the current regulator coupled to electrode 48A to increase the current sunk from 2.1 mA to 2.2 mA, for example. In some examples, processor 50 may adjust the step size based on the change in the measured voltage. For instance, if the increase from 2.0 mA to 2.1 mA caused the voltage measured at electrode 48A to increase from 3V to 3.1V, processor 50 may control the current regulator to increase the step size of the current increase from 0.1 mA to 0.25 mA.

Once processor 50 and measurement module 51 determine the current that is required to be sunk by the current regulator coupled to electrode 48A in order to produce a voltage of 4V at electrode 48A, processor 50 and measurement module 51 determine the current required to be sunk by the current regulator coupled to electrode 48B in order to produce a voltage of 5V at electrode 48A. In the example above, the voltage at electrode 48B is 6V. As such, the current regulator coupled to electrode 48B, under the control of processor 50, must decrease the amount of current it is sinking in order to reduce the voltage at electrode 48B from 6V to 5V. As the current regulator decreases the amount of current it is sinking, measurement module 51 measures the voltage at electrode 48B. Once measurement module 51 senses a voltage of 5V at electrode 48B, processor 50 controls the current regulator coupled to electrode 48B to continue to sink that particular amount of current, thereby maintaining 5V at electrode 48B (assuming that the load impedance does not change).

In some examples, rather than using an iterative process of driving current, then measuring, then driving current, and so forth in order to reach the specified voltage, processor 50 may calculate the necessary regulated currents using Ohm's law, the voltage measured at the selected electrode, and previously measured impedance values between the selected electrode and the common electrode. Then, processor 50 may control the respective current regulators to sink the calculated current. By eliminating at least some iterations by way of the calculated current, such example implementations may allow stimulator 4, for example, to more quickly adjust the stimulation to the desired voltage level(s).

In some examples, the measurement techniques described above may be combined. For example, processor 50 may control a current regulator to drive current and then measure the voltage at the respective electrode using measurement module 51. Then, processor 50 may accurately determine a step size by using the measured voltage and current delivered by the current regulator to determine an impedance. Using the determined impedance, processor 50 may then calculate the current required to produce the desired voltage at the selected electrode.

In other examples, measurement module 51 and processor 50 may monitor the voltage at a selected electrode and correct the voltage if it drifts outside predefined limits. Continuing the example above, measurement module 51 may monitor electrode 48A and if the voltage drifts more than 1% above or below the user specified voltage of 4V, processor 50 may control the current regulator coupled to electrode 48A to increase or decrease the amount of current that it is sinking in order to bring it back to within the 1% range. For example, if the voltage at electrode decreases to 3.8V, or 5% below the specified voltage of 4V, then processor 50 may control the current regulator coupled to electrode 48A to sink more current in order to increase the voltage to within +/−1% of the specified voltage of 4V. In this manner, measurement module 51 and processor 50 may continuously or periodically monitor the voltage at one or more selected electrodes and then drive the current of an associated current regulator in one direction or another to bring the voltage at the electrode back to within a specified range.

It should be noted that newly implanted stimulation leads may have greater impedance than leads that have been implanted for some time, e.g., several days or months. Generally, during the first few hours or days of use, the impedance of the stimulation leads will decrease. If the impedances of the selected electrodes change proportionally, the stimulation settings may not need to be adjusted in order to maintain the same stimulation. However, if the impedances of the selected electrodes do not change proportionally, in particular the electrodes programmed as cathodes, the stimulation settings may need to be adjusted in order to compensate for the changes. As such, measurement module 51 and processor 50 may periodically determine the impedances between selected electrodes and common electrodes and automatically adjust stimulation settings in order to account for changing impedances.

Depending on how long the leads have been implanted, measurement module 51 may sample at longer intervals. For instance, measurement module 51 may initially have a sampling rate of one or two seconds immediately after the stimulation leads have been implanted, but the sampling rate may increase to once every minute or hour if the leads have been implanted for several days or weeks. In some examples, processor 50 stores samples in memory 52 and analyzes the samples periodically in order to detect trends. If the trend flattens, processor 50 may determine that the lead impedances are not changing significantly. As such, processor 50 may instruct measurement module 51 to monitor signals on a daily basis, weekly basis, monthly basis, or the like.

In the manner describe above, a user may specify a voltage level for an electrode carried by an implanted medical lead coupled to an implantable medical device. A regulated current may be determined, e.g., by the implantable medical device or a programmer, for a regulated current path in order to produce the specified voltage level at the electrode. The implantable medical device may then deliver the determined regulated current via the regulated current path, thus producing the specified voltage at the electrode by a current-controlled system. The system is running in voltage mode, despite the fact that stimulation generator 60 is a current stimulation engine configured to operate in current mode, because the current produced by the current regulators is periodically or continuously adjusting, e.g., autoadjusting via firmware or the like, in order to meet the voltage specified at the selected electrode(s). Thus, using various techniques of this disclosure, a current mode system may emulate a voltage mode system.

Telemetry module 56 may include a radio frequency (RF) transceiver to permit bi-directional communication between implantable stimulator 4 and each of clinician programmer 20 and patient programmer 22. Telemetry module 56 may include an antenna 57 that may take on a variety of forms. For example, antenna 57 may be formed by a conductive coil or wire embedded in a housing associated with medical device 4. Alternatively, antenna 57 may be mounted on a circuit board carrying other components of implantable stimulator 4 or take the form of a circuit trace on the circuit board. In this way, telemetry module 56 may permit communication with clinician programmer 20 and patient programmer 22 in FIG. 1 or external programmer 40 in FIG. 2, to receive, for example, new programs or program groups, or adjustments to programs or program groups.

Power source 54 may be a non-rechargeable primary cell battery or a rechargeable battery and may be coupled to power circuitry. However, the disclosure is not limited to examples in which the power source is a battery. In another example, power source 5 may comprise a supercapacitor. In some examples, power source 54 may be rechargeable via induction or ultrasonic energy transmission, and include an appropriate circuit for recovering transcutaneously received energy. For example, power source 54 may be coupled to a secondary coil and a rectifier circuit for inductive energy transfer. In additional examples, power source 54 may include a small rechargeable circuit and a power generation circuit to produce the operating power. Recharging may be accomplished through proximal inductive interaction between an external charger and an inductive charging coil within stimulator 4. In some examples, power requirements may be small enough to allow stimulator 4 to utilize patient motion at least in part and implement a kinetic energy-scavenging device to trickle charge a rechargeable battery. A voltage regulator may generate one or more regulated voltages using the battery power.

Figure 4:
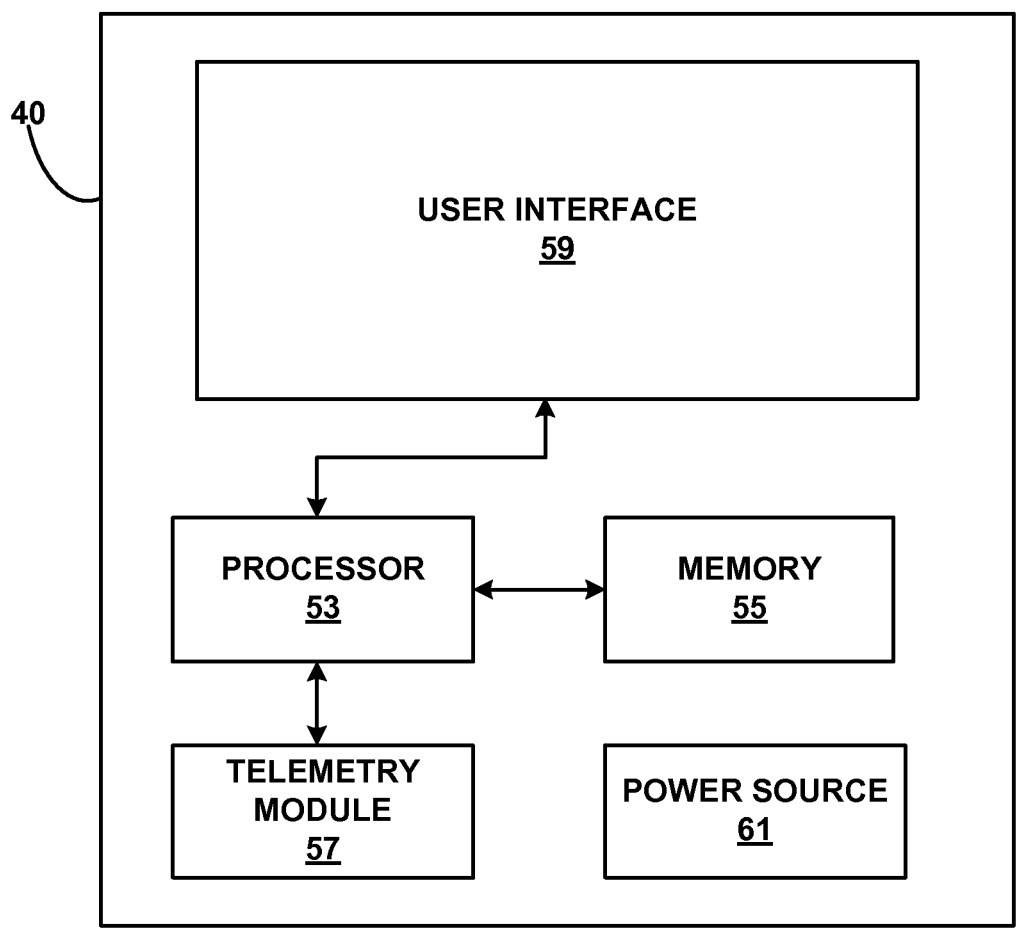
FIG. 4 is a block diagram illustrating various example components of an external programmer.

FIG. 4 is a functional block diagram illustrating various components of an external programmer 40 for an implantable stimulator 14. Although the components shown in FIG. 4 are described in reference to external programmer 40, the components may also be included within clinician programmer 20 or patient programmer 22 shown in FIG. 1. As shown in FIG. 4, external programmer 40 includes processor 53, memory 55, telemetry module 57, user interface 59, and power source 61. In general, processor 53 controls user interface 59, stores and retrieves data to and from memory 55, and controls transmission of data with implantable stimulator 34 through telemetry module 57. Processor 53 may take the form of one or more microprocessors, controllers, DSPs, ASICS, FPGAs, or equivalent discrete or integrated logic circuitry. The functions attributed to processor 53 in this disclosure may be embodied as software, firmware, hardware or any combination thereof.

Memory 55 may store instructions that cause processor 48 to provide various aspects of the functionality ascribed to external programmer 40 herein. Memory 55 may include any fixed or removable magnetic, optical, or electrical media, such as RAM, ROM, CD-ROM, magnetic disks, EEPROM, or the like. Memory 55 may also include a removable memory portion that may be used to provide memory updates or increases in memory capacities. A removable memory may also allow patient data to be easily transferred to another computing device, or to be removed before programmer 40 is used to program therapy for another patient. Memory 55 may also store information that controls operation of implantable stimulator 4, such as therapy delivery values.

A clinician or patient 36 interacts with user interface 59 in order to, for example, manually select, change or modify programs, adjust voltage or current amplitude, provide efficacy feedback, or view stimulation data. User interface 59 may include a screen and one or more input buttons that allow external programmer 40 to receive input from a user. The screen may be a liquid crystal display (LCD), plasma display, dot matrix display, or touch screen. The input buttons may include a touch pad, increase and decrease buttons, emergency shut off button, and other input media needed to control the stimulation therapy. User interface 59 may receive input from a user adjusting the voltage at one or more selected electrodes. Using the techniques described in this disclosure, processor 53 or processor 50 may determine the regulated current needed to produce the desired voltage at the selected electrode(s).

Telemetry module 57 allows the transfer of data to and from stimulator 34. Telemetry module 57 may communicate automatically with stimulator 34 at a scheduled time or when the telemetry module detects the proximity of the stimulator. Alternatively, telemetry module 57 may communicate with stimulator 34 when signaled by a user through user interface 59. To support RF communication, telemetry module 44 may include appropriate electronic components, such as amplifiers, filters, mixers, encoders, decoders, and the like.

Programmer 40 may communicate wirelessly with implantable stimulator 34 using, for example, RF communication or proximal inductive interaction. This wireless communication is possible through the use of telemetry module 44 which may be coupled to an internal antenna or an external antenna. Telemetry module 44 may be similar to telemetry module 57 of implantable stimulator 34.

Programmer 40 may also be configured to communicate with another computing device via wireless communication techniques, or direct communication through a wired, e.g., network, connection. Examples of local wireless communication techniques that may be employed to facilitate communication between programmer 24 and another computing device include RF communication based on the 802.11 or Bluetooth specification sets, infrared communication, e.g., based on the IrDA standard.

Power source 46 delivers operating power to the components of programmer 40. Power source 46 may be a rechargeable battery, such as a lithium ion or nickel metal hydride battery. Other rechargeable or conventional batteries may also be used. In some cases, external programmer 40 may be used when coupled to an alternating current (AC) outlet, i.e., AC line power, either directly or via an AC/DC adapter. Power source 61 may include circuitry to monitor power remaining within a battery. In this manner, user interface 59 may provide a current battery level indicator or low battery level indicator when the battery needs to be replaced or recharged. In some cases, power source 61 may be capable of estimating the remaining time of operation using the current battery.

Figure 5:
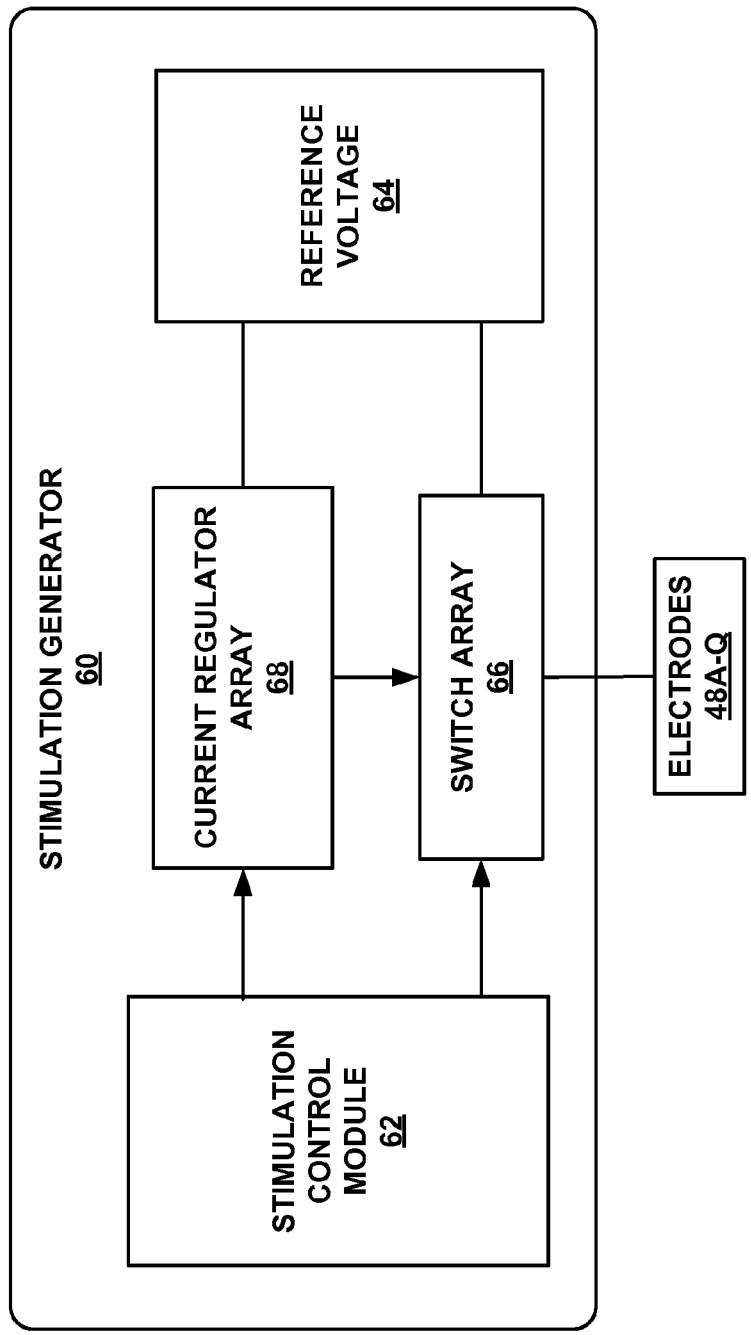
FIG. 5 is a block diagram illustrating various components of an example electrical stimulation generator for use in the implantable electrical stimulator of FIG. 3.

FIG. 5 is a block diagram illustrating various components of example stimulation generator 60. Stimulation generator 60 may be used with an implantable stimulator, e.g., to perform the functions of stimulation generator 60 as described with reference to FIGS. 1-3. Although described with respect to implantable stimulator 4, stimulation generator 60 may also be used for implantable stimulator 34, or other types of stimulators, including external stimulators of the type used during a "trialing" procedure. In the example of FIG. 5, stimulation generator 60 is selectively, e.g., based on a signal from processor 50 (FIG. 3), configured to deliver controlled-current stimulation pulses to patient 6 via various electrode combinations. In other examples, stimulation generator 60 may provide continuous, regulated current waveforms, rather than regulated current pulses. In still other examples, stimulation generator 60 may deliver combinations or continuous current waveforms and current pulses, or selectively deliver either continuous current waveforms or current pulses.

In the example illustrated in FIG. 5, stimulation generator 60 includes stimulation control module 62, reference voltage source 64, switch array 66, and current regulator array 68. Reference voltage source 64 may provide operating power to current regulator array 68, and may include a regulated voltage that sets the level of the reference voltage. As shown in FIG. 5, reference voltage source 64 may be coupled to provide operating power for the current regulator array 68 and provide a reference voltage for connection to electrodes 48A-48Q for an unregulated mode of electrode operation. In other examples, however, the voltage level of the reference voltage and the operating voltage level provided to regulated current source array 68 may be different.

Stimulation control module 62 forms a stimulation controller that controls switch array 66 and current regulator array 68 to deliver stimulation via electrodes 48A-48Q. Stimulation control module 62 may include one or more microprocessors, microcontrollers, digital signal processors (DSPs), application-specific integrated circuits (ASICs), field-programmable gate arrays (FPGAs), or other integrated or discrete logic circuitry. In operation, stimulation control module 62 may control delivery of electrical stimulation according to one or more programs that may specify stimulation parameters such as electrode combination, electrode polarity, stimulation current amplitude, pulse rate, and/or pulse width. Programs may be defined by a user via an external controller and downloaded to an implantable stimulator 4 or 34 for use by stimulation control module 62.

Current regulator array 68 includes a plurality of regulated current sources or sinks Again, a current regulator may function as either a current source or sink, or be selectively configured to operate as either a source or a sink. For convenience, however, the term "current regulator" may be used in some instances to refer to either a source or sink. Hence, each of the current regulators in current regulator array 68 may operate as a regulated current source that delivers stimulation via a corresponding one of electrodes 48A-Q or a regulated current sink that receives current from a corresponding one of electrodes 48A-Q, where electrodes 48A-48Q may be provided on leads, on a stimulator housing, on a leadless stimulator, or in other arrangements. In general, electrodes 48A-48Q may be referred to below as electrodes 48 for conciseness.

In some examples, each current regulator may include generally parallel source and sink circuits that can be individually selected to source or sink regulated current, or a single configurable circuit that can be configured to source or sink regulated current. In either case, for this example, each current regulator in current regulator array 68 may be considered bi-directional in the sense that it may deliver (source) or receive (sink) regulated current. Thus, each current regulator of regulated current source array 68 may be referred to as a regulated bidirectional current regulator. The regulated bidirectional current sources of current regulator array 68 may be configured as current mirrors that receive an input voltage from regulated reference voltage 64 or another supply voltage and output a substantially constant current value in response to the input voltage. The output current value may be programmable and may be controlled by a stimulation controller such as stimulation control module 62.

Each switch of switch array 66 couples a corresponding one of electrodes 48 to either a corresponding bidirectional current regulator of current regulator array 68 or to reference voltage 64. Stimulation control module 62 selectively opens and closes switches in switch array 66 to configure two or more of electrodes 48 as regulated electrodes by connection to regulated current sources or sinks in current regulator array 68 and one or more of electrodes 48 as unregulated electrodes by connection to reference voltage 64. In addition, stimulation control module 62 may selectively control individual regulated current sources or sinks in current regulator array 68 to deliver stimulation current pulses to the selected electrodes.

Reference voltage 64 may be a high or low voltage supplied by a regulated power source, depending on whether an electrode is programmed to be an unregulated source (high voltage rail) or unregulated sink (low voltage rail). Hence, reference voltage 64 may produce high and low reference voltages for selective coupling to unregulated, reference electrodes as needed given the selected electrode configuration. A regulated power source may produce one or more regulated voltage levels for use as reference voltage 64 and for use as a power rail for current regulator array 68. Again, although the same reference voltage 64 is coupled to current regulator array 68 in FIG. 5, different voltage levels could be used for the reference voltage coupled to switch array 66 and the operating voltage level provided to the regulated current source array. A regulated power source may generate the regulated voltages from voltages provided by a power source 54 (FIG. 3), such as a battery.

Continuing the example above in which a user selected electrodes 48A-48C to deliver stimulation therapy, stimulation control module 62 may open first and second switches of switch array 66 in order to couple electrodes 48A, 48B to regulated current sinks in current regulator array 68. Stimulation control module 62 may also close a third switch of switch array 66 in order to couple electrode 48C to reference voltage 64. The remaining switches of switch array 66 may be opened. The opening and closing of switches is described in more detail below in reference to FIG. 6.

In some cases, a regulated power source may be configured to generate multiple regulated voltage levels for use by different components within implantable stimulator 4, e.g., using a so-called voltage regulator stack. The voltage level delivered to current regulator array 68 by reference voltage 64 as a supply rail may be produced by a capacitor module that is charged for generation and delivery of a supply voltage for generation of a stimulation signal. The voltage level may be programmable and may be selected to provide sufficient headroom for operation of the regulated current sources. The voltage level provided by reference voltage 64 may be selected to provide an appropriate potential for generation of desired stimulation currents in conjunction with current regulator array 68. In general, the voltage levels produced by a regulated power source, including reference voltage 64, are not current regulated. Although the voltage levels produced by a regulated power source are constant, the current levels sourced or sunk with respect to such voltage levels may vary as a function of load. Hence, because reference voltage 64 is voltage-regulated but not current-regulated, switches in switch array 66 may selectively couple electrodes 48 to the reference voltage via unregulated current paths.

Stimulation control module 62 controls the operation of switch array 66 to produce electrode configurations defined by different stimulation programs. In some cases, the switches of switch array 66 may be metal-oxide-semiconductor field-effect-transistors (MOSFETs) or other circuit components used for switching electronic signals. The switches of switch array 66 may be designed to carry an amount of unregulated current that may be coupled to a corresponding electrode through an unregulated current path associated with reference voltage 64. As previously described, two or more regulated, stimulation electrodes 48 may be intentionally programmed to deliver different amounts of current such that the regulated electrodes produce an unbalanced current distribution.

One or more unregulated electrodes coupled to reference voltage 64 via respective switches in switch array 66 may balance the current distribution produced by the regulated electrodes via unregulated current paths. In some examples, each of the switches of switch array 66 may be capable of carrying a larger amount of current than a current regulator of current regulator array 68. To facilitate larger current carrying capacity, the sizes of the switches of switch array 66 may be larger than output transistors associated with the regulated current sources. The sizes of the switches may be selected according to desired current carrying capacity of a reference electrode.

To provide individual current control of electrodes 48 as either regulated electrodes or as unregulated electrodes, stimulation control module 62 controls operation of switch array 66, and current regulator array 68. When stimulation is delivered to patient 6, for the example of current pulses, stimulation control module 62 controls switch array 66 to couple selected stimulation electrodes for a desired electrode combination to respective current regulators of current regulator array 68 or to reference voltage 64, as needed. Stimulation control module 62 controls the regulated bidirectional current sources of current regulator array 68 coupled to regulated electrodes to source or sink specified amounts of current. For example, stimulation control module 62 may control selected current sources or sinks on a pulse-by-pulse basis to deliver current pulses to corresponding electrodes.

Stimulation control module 62 also deactivates the regulated bidirectional current regulators of current regulator array 68 tied to inactive electrodes, i.e., electrodes that are not active as regulated electrodes in a given electrode configuration. Each regulated bidirectional current regulator of current regulator array 68 may include an internal enable switch controlled by stimulation control module 62 that disconnects regulated power source 64 from the current regulator or otherwise disables the current source when the corresponding electrode is not used as a regulated electrode to deliver stimulation. Hence, configuration of electrodes 48A-48P may involve coordinated control of current regulator array 68 and switch array 66 to selectively activate current sources that are coupled to selected, regulated electrodes, selectively deactivate current sources that are coupled to electrodes that are either not selected or selected to be unregulated electrodes, and selectively couple and uncouple regulated and unregulated electrodes, respectively, to regulated current sources and reference voltage 64 via switch array 66.

Using stimulation generator 60 of FIG. 5, stimulator 4 or 34 may emulate a voltage mode system by selectively coupling one or more of a plurality of electrodes implanted within the patient to respective regulated current paths to deliver electrical stimulation current to the patient and selectively coupling at least another of the plurality of electrodes implanted within the patient to an unregulated current path to deliver the electrical stimulation current to the patient in response to receiving user input specifying a voltage level for the one or more electrodes selectively coupled to respective regulated current paths. Using the techniques described above, measurement module 51 and processor 50 (or processor 53) may determine a regulated current for each respective regulated current path in order to produce the specified voltage level at the one or more electrodes selectively coupled to the respective regulated current paths. Then, stimulation generator 60 may deliver the determined regulated currents via the respective regulated current paths.

FIG. 6 is a block diagram illustrating an example of various components of stimulation generator 60 shown in FIG. 5 in greater detail. In particular, FIG. 6 shows current regulator array 68 and switch array 66 in greater detail. As shown in FIG. 6, current regulator array 68 includes regulated bidirectional current regulators 68A-P and switch array 66 includes switches 78A-P and 79A-P. Each of bidirectional current regulators 68A-P includes a corresponding one of regulated current sources 72A-P that delivers regulated stimulation current to the corresponding electrode and a corresponding one of regulated current sinks 74A-P that receives regulated stimulation current from the corresponding electrode. Note that the block diagram illustrated in FIG. 6 is intended as a conceptual diagram that shows how stimulation generator 60 can be configured to control the operation of electrodes 48 in different modes, i.e., an off mode, regulated modes, and unregulated, reference modes. Thus, for ease of illustration, not all power and control signals are shown in FIG. 6.

In the example of FIG. 6, switches 78A-P may be coupled at one end to a high voltage reference, which may correspond to a high reference voltage level of reference voltage 64, and to a corresponding one of electrodes 48 at the other end. Switches 79A-P may be coupled at one end to a low voltage reference, which may correspond to low reference voltage level of reference voltage 64, and to a corresponding one of electrodes 48 at the other end. High reference voltage (High Vref) and low reference voltage (Low Vref) represent high and low voltage levels of reference voltage 64 (FIG. 5) and may be supplied by power source 54. For example, the high reference voltage may correspond to a reference voltage level and the low reference voltage may correspond to a ground potential to which the reference voltage level is referenced.

As further shown in FIG. 6, each regulated current source 72A-72P may be coupled to the high reference voltage or another upper voltage rail, which supports regulator overhead and sources current that is regulated by the regulated current source. In addition, each regulated current sink 74A-74P may be coupled to the low reference voltage or another lower voltage rail or ground potential, which supports regulator overhead and sinks current that is regulated by the regulated current sink.

Stimulation control module 62 controls the operation of regulated current sources 72A-72P, sinks 74A-74P, switches 78A-78P, and switches 79A-79P to configure electrodes 48A-48P as either inactive (i.e., off), regulated cathodes, regulated anodes, unregulated cathodes or unregulated anodes. For example, stimulation control module 62 may generate control signals to individually control regulated current sources 72A-72P to deliver specified amounts of regulated current to electrodes 48A-48P, respectively, and thereby configure such electrodes as regulated anodes. A can electrode 48Q may also be provided and coupled to regulated or unregulated current paths.

Similarly, stimulation control module 62 may generate control signals to individually control regulated current sinks 74A-74P to receive specified amounts of regulated currents from electrodes 48A-48P, respectively, and thereby configure such electrodes as regulated cathodes. For example, stimulation control module 62 may enable the current sources or sinks and also specify control voltages or current to be applied to the source or sinks to control the amount of current that is sourced or sunk via the respective electrodes 48A-48P.

In addition, stimulation control module 62 may generate control signals to control switches 78A-78P and 79A-79P to selectively couple electrodes 48A-48P to the high reference voltage or the low reference voltage, respectively.

For example, stimulation control module 62 may generate control signals Xah-Xph to close switches 78A-78P, respectively, and couple electrodes 48A-P to the high reference voltage. In this manner, electrodes 48A-P may be selectively configured as unregulated, reference anodes that source current from the high reference voltage. Similarly, stimulation control module 62 may generate control signals Xal-Xpl to close switches 79A-P, respectively, and couple electrodes 48A-P to the low reference voltage. In this manner, electrodes 48A-P may be selectively configured as unregulated, reference cathodes that sink current to the low reference voltage.

In general, an electrode 48A-48P may have one of five states: regulated cathode coupled to a regulated current sink 74A-74P, regulated anode coupled to a regulated current source 72A-72P, unregulated anode coupled to the high reference voltage, unregulated cathode coupled to the low reference voltage, or floating electrode not coupled to any circuit potential. Sources 72A-72P, sinks 74A-74P, switches 78A-78P, and switches 79A-79P are controlled by stimulation control module 62 such that only one of the above states is active for an electrode 48A-48P at a given time. For example, when electrode 48A operates as a regulated anode, regulated current source 72A is active, regulated current sink 74A is inactive, switch 78A is open and switch 79A is open. When a regulated source or sink is inactive, it may be in a high impedance state such that electrode 48A sees the source or sink as substantially an open circuit connection.

In an example implementation, each current regulator, in the form of either regulated current source 72A-72P or regulated current sink 74A-74P, may be implemented as a plurality of regulated current sources and sinks, respectively, operating in parallel to produce a combined, programmable current level sufficient for a desired stimulation therapy. A regulated current source 72A, for example, may be implemented by several parallel current sources (x N) having identical or similar structures. Similarly, a regulated current sink may be implemented by several parallel current sinks (x N) having identical or similar structures.

Hence, a regulated current source 72A may be implemented as N parallel, regulated current sources, each delivering a fraction of a total regulated current to be sourced by electrode 48A. Similarly, a regulated current sink 74A may be implemented as N parallel, regulated current sinks, each sinking a fraction of a total regulated to be sunk by electrode 48A. By activating a selected number of the parallel, regulated current sources forming a regulated current source 72A, stimulation control module 62 may control an amount of regulated source current delivered to a given electrode 48A coupled to the respective current source. Similarly, by activating a selected number of parallel, regulated current sink branches forming a regulated current sink 74A, stimulation control module 62 may control an amount of regulated sink current delivered from a given electrode 48A coupled to the respective current sink.

As an example, each current regulator, e.g., regulated source 72A-P or regulated sink 74A-P, may be implemented by N parallel current regulator branches. As an example, N may be equal to 64 in some implementations. In this type of implementation, stimulation control module 62 may specify a reference source current and a reference sink current, e.g., based on program data specified automatically or by a user via an external programmer. For each electrode, stimulation control module 62 may further specify a percentage of the reference source current or reference sink current to be delivered via the electrode, e.g., based on program data.

A control signal may be applied to each parallel current regulator branch such that the current levels produced by all N branches will add up to approximately the reference current level. Based on the percentage, which may be referred to as a gain ratio, stimulation control module 62 may selectively activate or deactivate a number of parallel current regulator branches for a given electrode sufficient to produce the specified percentage of the reference current. In this manner, stimulation control module 62 selectively scales up or scales down the number of active, parallel current regulator branches. If the reference current is 20 milliamps (mA), for example, the control signal is selected such that activation of all N parallel current regulator branches would produce 20 mA of source current or sink current, as applicable, for application via an electrode. In this case, the control signal may be selected such that each current regulator branch produces $1/N^{th}$ of the reference current.

If the percentage to be delivered by a given electrode is 50 percent, then stimulation control module 62 activates 50 percent of the N parallel current regulator branches or, conversely, deactivates 50 percent of the N parallel current regulator branches. In either case, N/2 parallel current regulator branches are activated, producing a combined current of 50%×20 mA=10 mA in this example. Hence, when activated, each current regulator may source or sink a finite amount of current, determined as a function of the control signal, such that the fractional currents flowing in the parallel regulator branches can be summed to produce an overall regulated current. If the reference current is changed, the applicable control signal applied to each current regulator branch is changed.

By specifying percentages of source current and sink current for respective electrodes, stimulation control module 62 can control current regulators 72A-72P and 74A-74B to precisely and selectively control the current levels sourced or sunk by particular electrodes 48A-48P. In addition, stimulation control module 62 can support effective steering of stimulation current to create different electrical stimulation fields or patterns useful in electrical stimulation therapy.

Using regulated current source 72A and electrode 48A as an example, the outputs of the parallel current source branches forming the regulated current source are coupled to electrode 48A such that the electrode receives a sum of the regulated source currents produced by the multiple, parallel current source branches. A similar arrangement can be provided for current sinks 74A-74P. Hence, the description of a single source or sink and the representation of a single source or sink in FIG. 6 are provided for purposes of illustration, and may represent either a single source or sink or multiple, parallel sources or sinks configured as described in this disclosure. Likewise, each switch 78A-78P, 79A-79P may be implemented by a single switch, or by multiple, parallel switches operating to support a sum of the multiple, fractional currents sourced or sunk via each parallel switch.

When turned "ON," each parallel current source or sink branch may produce a known amount of current, defined by the reference current and corresponding control signal, as described above. In this manner, a source or sink may be considered either ON or OFF, and deliver the same fractional amount of current as other sources or sinks whenever it is ON. Alternatively, in some examples, each parallel current source or sink could be configured to provide different fractional amounts of current, or deliver variable amounts of current according to a bias signal. Although it is understood that each given source 72A-72P or sink 74A-74P may include multiple, parallel source branches or sink branches, and that a given switch 78A-78P or 79A-79P may include multiple, parallel switches, this disclosure will generally refer to each of sources 72A-72P, sinks 74A-74P, or switches 78A-78P, 79A-79P on a singular basis for ease of illustration.

Continuing the example above in which a user selected electrodes 48A-48C to deliver stimulation therapy, processor 50, for example, controls stimulation control module 62 to generate control signals to open switches 78A and 79A, enable regulated current sink 74A, and disable regulated current source 72A. In this manner, electrode 48A is coupled to regulated current sink 74A. Similarly, to couple electrode 48B to regulated current sink 74B, processor 50 controls stimulation control module 62 to generate control signals to open switches 78B and 79B (not shown), enable regulated current sink 74B (not shown), and disable regulated current source 72B (not shown).

To couple electrode 48C to a high reference voltage as a common anode, stimulation control module 62 may generate control signal Xch (not shown) to close switch 78C (not shown) and couple electrode 48C to the high reference voltage. Measurement module 51 of FIG. 3 may monitor the signals at the selected electrodes 48A, 48B and, in response, processor 50 may determine the currents required to be sunk by regulated current sinks 74A, 74B to produce the user specified voltages, and then control stimulation control module 62 to adjust the currents sunk by regulated current sinks 74A, 74B.

Example schematic circuit diagrams that may be used to implement stimulation generator 60, regulated current sources 72A-72P, and regulated current sinks 74A-74P are shown and described in detail in U.S. patent application Ser. No. 12/579,036 to Torgerson et al., entitled "MEDICAL DEVICES AND METHODS FOR DELIVERY OF CURRENT-BASED ELECTRICAL STIMULATION THERAPY," the entire content of which is incorporated herein by reference.

Figure 7A:
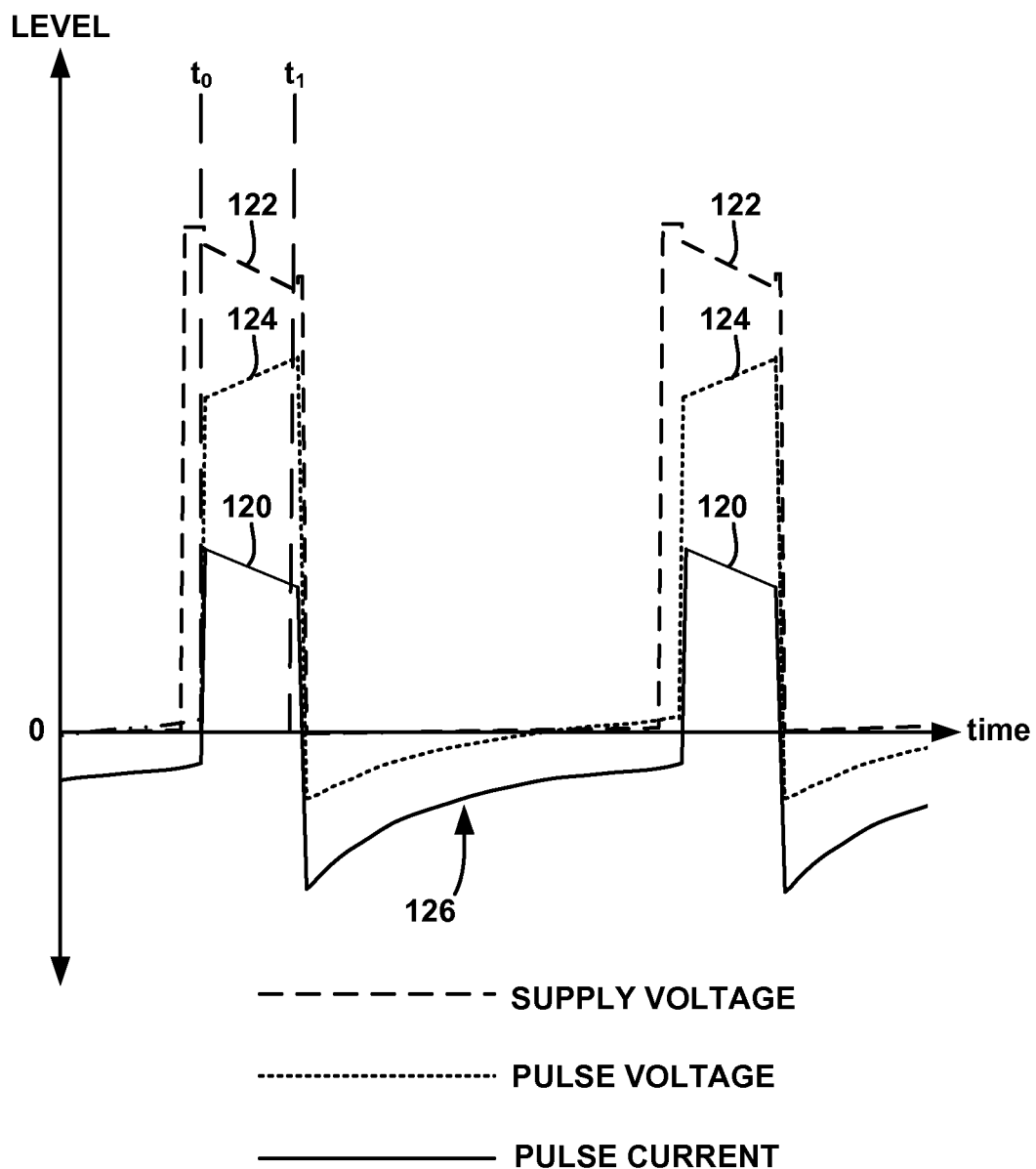
FIGS. 7A and 7B are graphs illustrating example stimulation pulses delivered according to examples of this disclosure.
Figure 7B:
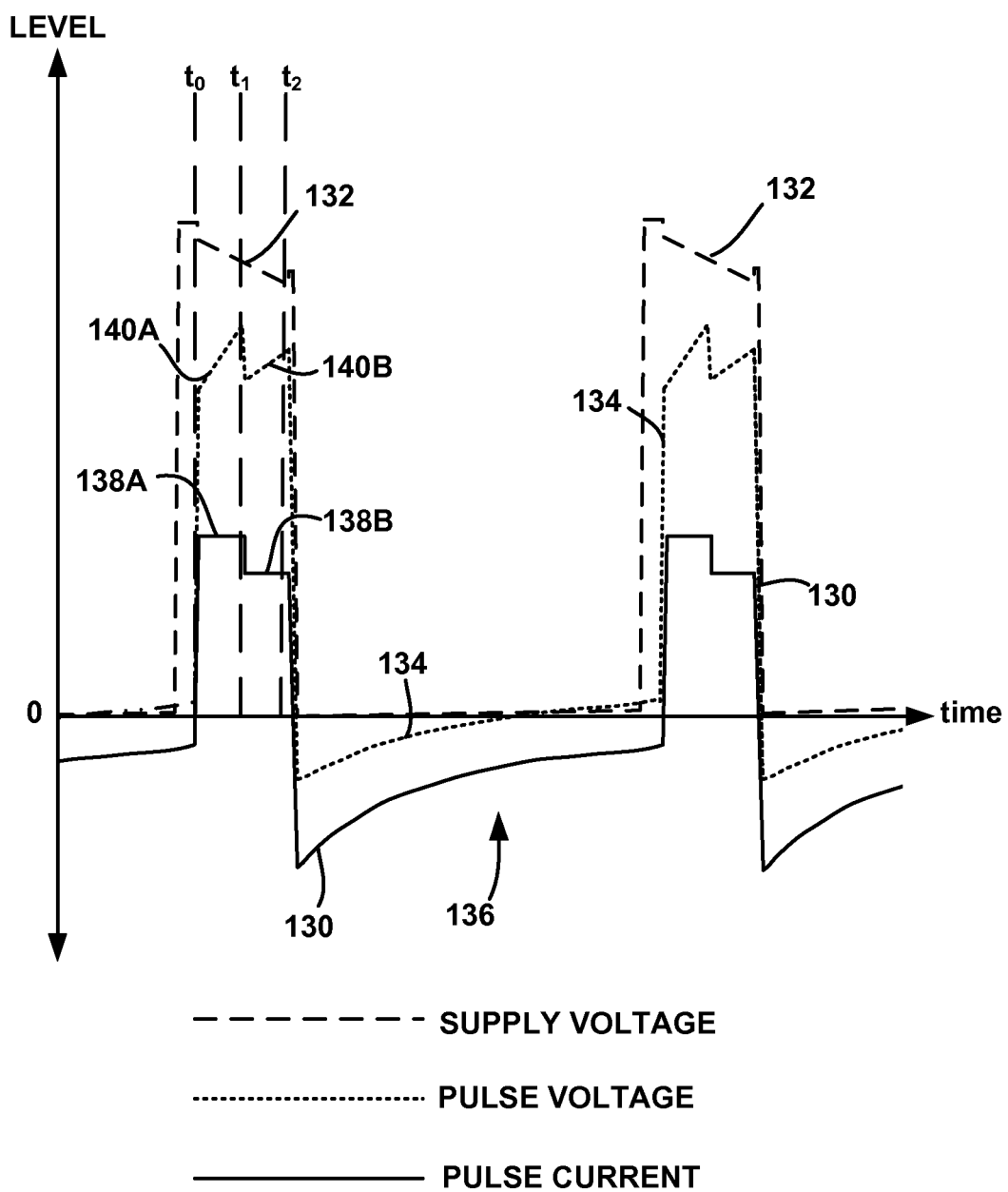

FIGS. 7A and 7B are graphs illustrating example stimulation pulses delivered according to one example of this disclosure. In FIGS. 7A and 7B, the horizontal axis represents time and the vertical axis represents current or voltage level. As shown in FIGS. 7A and 7B, the pulse current level may be controlled by stimulation generator 60 to decrease during the pulse width such that the sum of the pulse voltage level and the headroom voltage does not exceed a supply voltage level. In particular, the pulse current level can be controlled to decrease according to a decrease in the supply voltage level and an increase in voltage from the load capacitance during the pulse width. In this manner, the current stimulation pulse may have a higher current amplitude at the beginning of the pulse and a lower current value at the end of the pulse in order to more closely represent the current of a pulse delivered via a voltage mode system.

As an illustration, in some examples, the pulse current level may be controlled to have a decay profile, such as a linear slope, that is determined based on a decay, characterized by a decreasing slope, of the supply voltage level during the pulse width. In addition, the pulse current level may be controlled to have a decay profile that is determined based on an increase in load voltage due to charging of a load capacitance during the pulse width. In some cases, the pulse may comprise first and second sub-pulses. The second sub-pulse follows the first sub-pulse in time and has a pulse current level that is less than the pulse current level of the first sub-pulse. In other cases, the pulse may comprise more than two sub-pulses. The pulse current levels of the sub-pulses may be selected to have an average current level that is determined based on a decrease in the supply voltage level and an increase in the load voltage level.

For a given pulse, with a programmed current level, stimulation generator 60 may generate a decreasing pulse current level profile for a single pulse, or a set of sub-pulses with specified current levels to deliver the pulse. The profile and/or sub-pulse levels may correspond to a desired average current specified by the programmed current level, and may be determined using calculations by processor 50 of stimulator 34 (or stimulator 4), or processor 53 of programmer 40 (or programmer 20 or 22), or based on pre-stored mappings (e.g., pulse current level to sub-pulse current levels) in memory 52 of stimulator 34 (or stimulator 4), or in memory 55 of programmer 40 (or programmer 20 or 22).

In each case, the calculations or mappings may be generated based on calculations, measurement or knowledge of the actual discharge profile of the voltage supply and the increase profile of the load voltage, based on supply capacitance, load capacitance, load impedance, headroom voltage, and other characteristics such as pulse current level and pulse width. Knowledge of the voltage supply discharge profile and load voltage charge profile may be obtained in some examples, based on measurements taken, e.g., in a laboratory or in the factory, or by stimulator 4 or 34, for different voltage levels, current levels and pulse widths, to characterize the profiles.

In some examples, profile or sub-pulse determinations may be made within the IMD (e.g., stimulator 4 or 34) based on a current level specified by a program provided by programmer 20, 22, or 40, or possibly made within an external programmer such as one of programmers 20, 22, or 40 and conveyed to the IMD via telemetry, e.g., as sub-pulse current levels. Alternatively, as discussed above, such determinations may be pre-computed and stored as a mapping in memory of either stimulator 4 or 34, or any of programmers 20, 22, and 42.

In the example of FIG. 7A, the graph illustrates delivery of two successive stimulation current pulses, with a pulse current level represented by trace 120. The supply voltage level is represented by trace 122. The pulse voltage level is represented by trace 124 and a headroom voltage level is represented by the space between trace 122 (the supply voltage level) and trace 124 (the pulse voltage level). The headroom voltage level may be specified for a particular current regulator, based on the amount of voltage required by circuit components of the current regulator. In some examples, the headroom voltage level may include this voltage required by the circuit components plus a small margin voltage.

As shown in FIG. 7A, over a pulse width extending from time t0 to time t1, the pulse current level 120 decreases from an initial current level at time t0 to a reduced current level at time t1. Hence, the pulse current level decreases over the duration of the pulse width. After time t1, the pulse current level 120 and the pulse voltage level 124 drop and then recover during a passive recharge cycle, generally indicated by reference number 126. In some cases, an active recharge cycle may be applied instead of, or in addition to, a passive recharge cycle. During the delivery of each pulse, from t0 to t1, the level of a supply voltage 122 for the current regulator that delivers the pulse decreases, i.e., due to discharging of one or more capacitors associated with the voltage supply.

As the supply voltage level 122 decreases over the pulse width, the pulse voltage level 124 increases. As shown in FIG. 7A, however, the decrease in the pulse current level 120 is effective in maintaining the pulse voltage level 124 below the supply voltage level 122. If the pulse current level 120 was maintained at a constant level during the pulse width, it is possible that the pulse voltage level 124 could exceed the supply voltage level 122, penetrating the headroom of the current regulator, and undermining effective regulation of the pulse current level.

By reducing the pulse current level 120 over time, the pulse voltage level 124 does not rise as high as it otherwise could rise. Yet, the pulse current level 120, and the slope of the decrease, can be selected such that the pulse still delivers a desired average current level over the pulse width. As shown in the example of FIG. 7A, the average slope of the decrease in the pulse current level 120 could be selected to approximate the average slope of a decrease in the supply voltage level 122 if the voltage on the load capacitance was not taken into account. With the load voltage, however, the slope of pulse current level 120 may be different from the slope of supply voltage level 122. In some cases, the slope of the decrease in pulse current level 120 may be constant and linear, or may vary in a nonlinear manner.

The pulse current level 120 may be selectively controlled by stimulation generator 60 to output different current levels at different times during the duration of the pulse width. For example, stimulation generator 60 may control activation of a number of parallel current regulator branches or directly control a current delivered by a given current regulator in order to provide a pulse shape that decreases in current level from a start of the pulse width to an end of the pulse width, as shown in FIG. 7A. Hence, the pulse current level may be continuously controlled or controlled over a series of time slots or sub-pulses, as will be described in further detail with reference to the example of FIG. 7B. In either case, the current level may decrease over time to prevent the pulse voltage level from exceeding the supply voltage level.

With the decrease in the pulse current level 120, a higher average current can be delivered by stimulation generator 60 in a controlled manner without the need to increase the supply voltage level in order to prevent the pulse voltage level from exceeding the supply voltage level. By avoiding an increase in supply voltage level, the techniques described in this disclosure may, in some cases, permit longer battery life or longer time between recharges in the case of a rechargeable battery, as well as minimal or no effect on therapeutic outcome. In some cases, the voltage supply for the current regulator may use downsized capacitor values to generate the required pulse voltage, allowing the use of smaller electrical hybrid circuitry, smaller devices, or larger batteries.

In the example of FIG. 7B, the graph illustrates delivery of two successive stimulation current pulses, where each pulse is split, i.e., sub-divided, into first and second sub-pulses with different current levels. By splitting a pulse into sub-pulses with different current levels such that the current stimulation pulse has a higher current amplitude at the beginning of the pulse and a lower current value at the end of the pulse, the current stimulation pulse may more closely represent the current of a pulse delivered in voltage mode. As an example, the average pulse current level during the first and second sub-pulses may be selected and controlled by stimulation generator 60 such that the pulse voltage level for the regulator does not exceed the supply voltage level for the regulator during the pulse width. In FIG. 7B, pulse current level is represented by trace 130, supply voltage level is represented by trace 132, the pulse voltage level is represented by trace 134, and a headroom voltage level is represented by the space between trace 132 (the supply voltage level) and trace 134 (the pulse voltage level). A passive recharge cycle is generally indicated by reference numeral 136, although an active recharge could be used in some examples. Each pulse in the example of FIG. 7B, extending from time t0 to time t2, is divided into a first sub-pulse 138A and a second sub-pulse 138B. In other examples, multiple sub-pulses may be delivered for each pulse.

The second sub-pulse 138B follows the first sub-pulse 138 in time and has a pulse current level that is less than the pulse current level of the first sub-pulse. In this sense, the pulse delivered between time t0 and time t1 may be split into two portions: a higher current portion provided by sub-pulse 138A and a lower current portion provided by sub-pulse 138B. First sub-pulse 138A is delivered from time t0 to time t1, and second sub-pulse 138B is delivered from time t1 to time t2. Again, in other cases, the pulse may comprise more than two sub-pulses, such as high, medium and low portions, or a greater number of sub-pulses providing even greater granularity in current level. In general, the proportion of the higher current level or levels to the lower current level or levels may be determined based on the decrease of the supply voltage level 132 and an increase in a load voltage. For example, the pulse current levels of the sub-pulses 138A, 138B may be selected to produce an average current level that approximates a slope of the supply voltage level 134 during the pulse width from time t0 to time t1, as described above, if the contributions of the load capacitance are ignored. Alternatively, the average current level may be determined based on the negative slope on the supply voltage level and the positive slope of the voltage on the load capacitance during the pulse width.

As further shown in FIG. 7B, the different current levels of the first and second sub-pulses 138A, 138B may have an effect on the voltage levels of the sub-pulses. In particular, sub-pulse 138A may have a current level that produces a sum of the pulse voltage level and headroom voltage 140A from approximately time t0 to t1, and sub-pulse 138B may have a current level that produces a sum of pulse voltage level and headroom voltage 140B from approximately time t1 to t2. In general, as the load voltage increases, due to charging of the load capacitance, the pulse voltage level that is needed to maintain a desired, regulated pulse current level also needs to increase. As supply voltage level 132 drops and the required pulse voltage needs increase (as a result of an increase in the voltage on the load capacitance) between time t0 and t2, the delivery of the reduced current level for sub-pulse 138B limits the increase of the sum of the pulse voltage level and headroom voltage 140B so that the pulse voltage level, even though it increases, remains below supply voltage level 132, thereby preserving voltage overhead in the current regulator to prevent the pulse current level from going out of regulation.

In some cases, this approach may permit a smaller supply voltage to be used to deliver a stimulation current pulse with a desired average current level. As an illustration, assume that a voltage supply ordinarily would require an initial voltage level of 5 volts to support delivery of a given stimulation current pulse because the voltage supply would decay to 4.7 volts while the pulse voltage would rise to 4.5 volts, assuming a requirement for 0.2 volts of headroom voltage in the current regulator. If the stimulation current level is decreased over the pulse width while producing the same average current, but the resulting pulse voltage level rises to only 4.3 volts, then the voltage supply could have an initial value of only 4.8 volts. The reduced initial voltage requirement for the voltage supply in this scenario could permit the voltage supply to be constructed with reduced size capacitor module.

In the examples of FIGS. 7A and 7B, for purposes of illustration, the graphs illustrate anodic current pulses in which current levels and voltage levels are positive. However, the techniques described in this disclosure may be applied for both anodic and cathodic current pulses. In each case, the magnitude of the pulse current level may be decreased to prevent the magnitude of the pulse voltage level from exceeding the magnitude of the supply voltage level during the course of the pulse width. In other words, the pulse current level is controlled so that the absolute value of the pulse voltage level does not exceed the absolute value of the supply voltage level.

As discussed above, multiple sub-pulses may be used to deliver a pulse waveform having a current level that decreases over the course of its pulse width. In some cases, delivery of two sub-pulses for each pulse may be effective and even desirable. If stimulation generator 60 includes a redundant current regulator for each electrode, for example, one current regulator could be used to deliver a first sub-pulse and a second regulator could be used to deliver a second sub-pulse that follows the first sub-pulse in time and has a current level that is less than a current level of the first sub-pulse. The current regulators may be triggered by control signals at time t0 and t1, respectively, or the second current regulator may be triggered based on a delay running from the time the first current regulator is activated.

Splitting a stimulation current pulse into sub-pulses may be performed in a variety of ways. As described above, the sub-pulses may have different current levels and either equal or nonequal sub-pulse widths. The current level for each sub-pulse is substantially constant for the duration of the respective sub-pulse width. Splitting a stimulation pulse into two sub-pulses with different stimulation current levels allows a pulse with the same total charge to be delivered while requiring less voltage on the supply capacitor module associated with the voltage supply, which may be formed by a capacitor stack with a selectable number of capacitors, but which will be referred to generally below as a supply capacitor for convenience. As an example, instead of delivering a 3 milliamp (mA) constant current pulse, a pulse may be subdivided into a first sub-pulse with a first sub-pulse width and a current level of 3.5 mA and a second sub-pulse with a second sub-pulse width equal to the first sub-pulse with and a current level of 2.5 mA, resulting in an average current of 3 mA, which is equal to the average current of the desired 3 mA constant current pulse. Several example techniques that may be used for determining current levels for two sub-pulses forming an overall pulse are described in detail in U.S. patent application Ser. No. 12/603,316 to Straka et al., entitled "ELECTRICAL STIMULATION THERAPY USING DECAYING CURRENT PULSES," the entire content of which is incorporated herein by reference.

Figure 8:
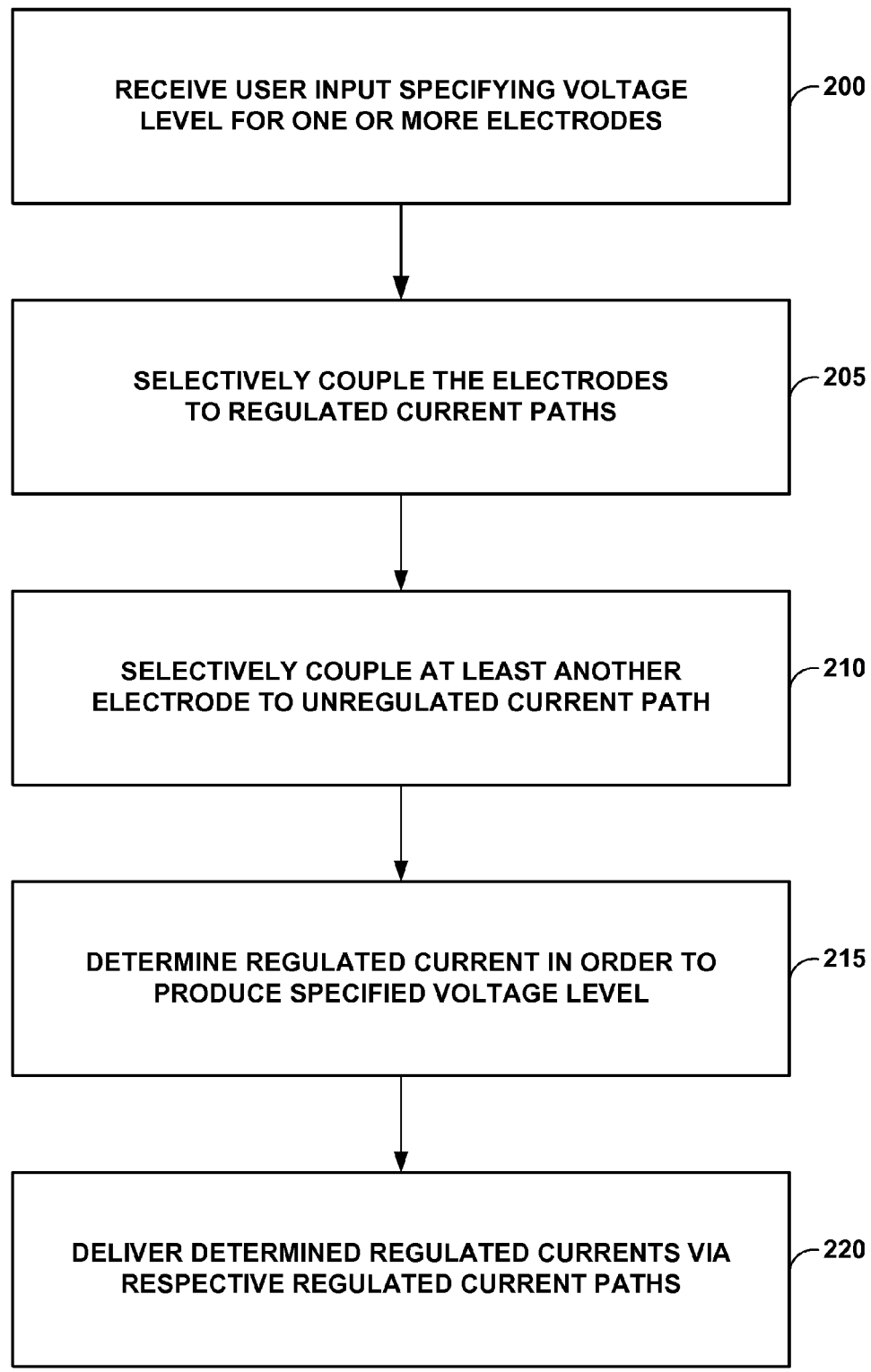
FIG. 8 is a flow diagram illustrating an example method for emulating a voltage mode system using a current mode system in accordance with certain techniques of this disclosure.

FIG. 8 is a flow diagram illustrating an example method for emulating a voltage mode system using a current mode system in accordance with certain techniques of this disclosure. A programmer, e.g., a clinician programmer or patient programmer, receives user input specifying a voltage level for one or more electrodes implanted within a patient (200). Processor 50, for example, controls stimulation control module 62 to selectively couple the one or more electrodes to respective current paths to deliver electrical stimulation current to the patient (205), and to selectively couple at least another electrode implanted within the patient to an unregulated current path to deliver electrical stimulation current to the patient (210). In this manner, one or more electrodes are configured as regulated electrodes to source or sink current via one or more respective current regulators, and at least one other electrode is configured to act as a common electrode to sink or source current to a low or high reference voltage. Measurement module 51 monitors the voltage at the one or more electrodes and processor 50 determines the regulated current for each respective current path based on the monitored voltage in order to produce the specified voltage level at the one or more electrodes selectively coupled to the respective current paths (215).

In some examples, processor 50 determines the regulated current by calculating the current required, as described above, and setting a respective regulator to the calculated current. In other examples, processor 50 determines the current by monitoring the voltage at an electrode via measurement module 51, adjusts the amount of current sourced or sunk by a respective current regulator, monitors the voltage at the electrode, and so forth, without an explicit calculation of the current required. Once the current is determined, processor 50 controls stimulation generator 60 to deliver the determined regulated currents via the respective regulated current paths.

In some example implementations, coupling includes coupling a first electrode to a first regulated current path to deliver a first amount of the electrical stimulation current, coupling a second electrode to a second regulated current path to deliver a second amount of the electrical stimulation current, and coupling a third electrode to the unregulated current path to deliver a third amount of the electrical stimulation current approximately equal to a sum of the first and second amounts of the electrical stimulation current, wherein the unregulated current path is coupled to a reference voltage.

In one example determining a regulated current for each respective regulated current path in order to produce the specified voltage level at the one or more electrodes selectively coupled to the respective regulated current paths comprises delivering a first electrical current via a first electrode of the one or more electrodes selectively coupled to the respective regulated current paths, measuring a voltage difference value between the first electrode and one of the plurality of electrodes coupled to an unregulated current path, calculating an impedance value between the first electrode and the one of the plurality of electrodes coupled to an unregulated current path based on the first electrical current and the measured voltage difference value, and determining the regulated current based on the calculated impedance value.

In another example, determining a regulated current for each respective regulated current path in order to produce the specified voltage level at the one or more electrodes selectively coupled to the respective regulated current paths comprises delivering a first electrical current via a first electrode of the one or more electrodes selectively coupled to the respective regulated current paths, measuring a voltage at the first electrode, and adjusting the first electrical current in response to the measured voltage.

In one example, delivering the determined regulated currents via the respective regulated current paths comprises generating one of the determined regulated currents via a respective current regulator, the one of the determined regulated currents having a pulse current level, a pulse voltage level, and a pulse width, controlling the pulse current level to decrease during the pulse width, and delivering the one of the determined regulated currents pulse via one or more implantable electrodes. In some examples, generating one of the determined regulated currents via a respective current regulator comprises generating one of the determined regulated currents having first and second sub-pulses, the second sub-pulse following the first sub-pulse in time, wherein the pulse current level of the second sub-pulse is less than the pulse current level of the first sub-pulse.

Various aspects of the disclosure have been described. These and other aspects are within the scope of the following claims.

The invention claimed is:

1. A method for controlling a system for delivering electrical stimulation therapy, the method comprising:
   receiving user input specifying a voltage level of electrical stimulation to be delivered by one or more of a plurality of electrodes of the system, wherein the electrodes are implanted within the patient;
   selectively coupling, by a stimulation controller of a stimulation generator of the system, the one or more electrodes to respective regulated current paths to deliver the electrical stimulation to the patient;
   selectively coupling, by the stimulation controller, at least another of the plurality of electrodes implanted within the patient to an unregulated current path to deliver the electrical stimulation to the patient;
   generating, by one or more current regulators of the stimulation generator of the system, regulated currents for the regulated current paths;
   determining, by a processor of the system, the regulated current for each respective regulated current path in order to produce the specified voltage level at the one or more electrodes selectively coupled to the respective regulated current paths such that the system emulates a voltage mode system; and
   controlling, by the processor, the stimulation generator to deliver the determined regulated currents via the respective regulated current paths.

2. The method of claim 1,
   wherein selectively coupling the one or more electrodes to respective regulated current paths to deliver the electrical stimulation to the patient comprises:
   coupling a first electrode to a first regulated current path to deliver a first amount of the electrical stimulation current; and
   coupling a second electrode to a second regulated current path to deliver a second amount of the electrical stimulation current, and
   wherein selectively coupling at least another of the plurality of electrodes implanted within the patient to an unregulated current path to deliver the electrical stimulation to the patient comprises:
   coupling a third electrode to the unregulated current path to deliver a third amount of the electrical stimulation current approximately equal to a sum of the first and second amounts of the electrical stimulation current, wherein the unregulated current path is coupled to a reference voltage.

3. The method of claim 1, wherein at least some of the plurality of electrodes are carried by one or more leads implanted within the patient.

4. The method of claim 1, further comprising coupling the electrodes to the regulated and unregulated current paths on a selective basis to form different electrode configurations.

5. The method of claim 1, wherein determining a regulated current for each respective regulated current path in order to produce the specified voltage level at the one or more electrodes selectively coupled to the respective regulated current paths comprises:
   delivering a first electrical current via a first electrode of the one or more electrodes selectively coupled to the respective regulated current paths;
   measuring a voltage difference value between the first electrode and one of the plurality of electrodes coupled to the unregulated current path;
   calculating an impedance value between the first electrode and the one of the plurality of electrodes coupled to an unregulated current path based on the first electrical current and the measured voltage difference value; and
   determining the regulated current based on the calculated impedance value.

6. The method of claim 1, wherein determining a regulated current for each respective regulated current path in order to produce the specified voltage level at the one or more electrodes selectively coupled to the respective regulated current paths comprises:
   delivering a first electrical current via a first electrode of the one or more electrodes selectively coupled to the respective regulated current paths;
   measuring a voltage at the first electrode; and
   adjusting the first electrical current in response to the measured voltage.

7. The method of claim 1, wherein delivering the determined regulated currents via the respective regulated current paths comprises:
   generating one of the determined regulated currents via a respective current regulator, the one of the determined regulated currents having a pulse current level, a pulse voltage level, and a pulse width;
   controlling the pulse current level to decrease during the pulse width; and
   delivering the one of the determined regulated currents pulse via one or more implantable electrodes.

8. The method of claim 7, wherein generating one of the determined regulated currents via a respective current regulator comprises generating one of the determined regulated currents having first and second sub-pulses, the second sub-pulse following the first sub-pulse in time, wherein the pulse current level of the second sub-pulse is less than the pulse current level of the first sub-pulse.

9. A system for delivering electrical stimulation therapy, the system comprising:
   a plurality of implantable electrodes;
   a stimulation generator comprising:
      a stimulation controller configured to:
         selectively couple one or more of the plurality of implantable electrodes to respective regulated current paths to deliver electrical stimulation to a patient, and
         selectively couple at least another of the plurality of implantable electrodes to an unregulated current path to deliver the electrical stimulation to the patient; and
      one or more current regulators configured to generate regulated currents for the regulated current paths; and a processor configured to:
  receive user input from a user specifying a voltage level of the electrical stimulation to be delivered by the one or more of the plurality of electrodes;
  determine the regulated current for each respective regulated current path in order to produce the specified voltage level at the one or more electrodes selectively coupled to the respective regulated current paths such that the system emulates a voltage mode system; and
  control the stimulation generator to deliver the determined regulated currents via the one or more current regulators and the respective regulated current paths.

10. The system of claim 9,
  wherein the stimulation controller configured to selectively couple the one or more electrodes to respective regulated current paths to deliver the electrical stimulation to the patient is further configured to:
  couple a first electrode to a first regulated current path to deliver a first amount of the electrical stimulation current; and
  couple a second electrode to a second regulated current path to deliver a second amount of the electrical stimulation current, and
  wherein the stimulation controller configured to selectively couple at least another of the plurality of electrodes implanted within the patient to an unregulated current path to deliver the electrical stimulation to the patient is further configured to:
  couple a third electrode to the unregulated current path to deliver a third amount of the electrical stimulation current approximately equal to a sum of the first and second amounts of the electrical stimulation current, wherein the unregulated current path is coupled to a reference voltage.

11. The system of claim 9, wherein at least some of the plurality of electrodes are carried by one or more leads implanted within the patient.

12. The system of claim 9, wherein the stimulation controller is further configured to couple the electrodes to the regulated and unregulated current paths on a selective basis to form different electrode configurations.

13. The system of claim 9, wherein the processor configured to determine the regulated current for each respective regulated current path in order to produce the specified voltage level at the one or more electrodes selectively coupled to the respective regulated current paths is further configured to:
  control the stimulation generator to deliver a first electrical current via a first electrode of the one or more electrodes selectively coupled to the respective regulated current paths;
  control measurement of a voltage difference value between the first electrode and one of the plurality of electrodes coupled to the unregulated current path;
  calculate an impedance value between the first electrode and the one of the plurality of electrodes coupled to an unregulated current path based on the first electrical current and the measured voltage difference value; and
  determine the regulated current based on the calculated impedance value.

14. The system of claim 9, wherein the processor configured to determine the regulated current for each respective regulated current path in order to produce the specified voltage level at the one or more electrodes selectively coupled to the respective regulated current paths is further configured to:
  control the stimulation generator to deliver a first electrical current via a first electrode of the one or more electrodes selectively coupled to the respective regulated current paths;
  control measurement of a voltage at the first electrode; and
  control the stimulation generator to adjust the first electrical current in response to the measured voltage.

15. The system of claim 9, wherein the processor configured to control the stimulation generator to deliver the determined regulated currents via the one or more current regulators and the respective regulated current paths is further configured to:
  control the stimulation generator to generate one of the determined regulated currents via a respective one of the current regulators, the one of the determined regulated currents having a pulse current level, a pulse voltage level, and a pulse width;
  control the stimulation generator to control the pulse current level to decrease during the pulse width; and
  control the stimulation generator to deliver the one of the determined regulated currents via one or more implantable electrodes.

16. The system of claim 15, wherein the processor configured to control the stimulation generator to generate one of the determined regulated currents via the respective current regulator is further configured to control the stimulation generator to generate one of the determined regulated currents having first and second sub-pulses, the second sub-pulse following the first sub-pulse in time, wherein the pulse current level of the second sub-pulse is less than the pulse current level of the first sub-pulse.

17. A device for delivering electrical stimulation therapy, the device comprising:
  means for receiving user input specifying a voltage level of electrical stimulation to be delivered by one or more of a plurality of electrodes implanted within the patient;
  means for selectively coupling the one or more electrodes to respective regulated current paths to deliver the electrical stimulation to the patient;
  means for selectively coupling at least another of the plurality of electrodes implanted within the patient to an unregulated current path to deliver the electrical stimulation to the patient;
  means for determining a regulated current for each respective regulated current path in order to produce the specified voltage level at the one or more electrodes selectively coupled to the respective regulated current paths such that the device emulates a voltage mode device;
  means for generating the regulated current for each respective regulated current path; and
  means for delivering the determined regulated currents via the respective regulated current paths.

18. The system of claim 9, wherein the processor is configured to determine the regulated current to produce the specified voltage level based on a measured voltage at one of the electrodes.

19. The system of claim 18, wherein the processor is configured to control measurement of the measured voltage during delivery of the regulated current.

20. The system of claim 9, wherein the processor is configured to determine the regulated current to produce the specified voltage level based on an impedance measured between two of the electrodes.

21. The system of claim 20, wherein the processor is configured to control measurement of the measured impedance during delivery of the regulated current.

22. The system of claim 9, wherein the at least another of the plurality of electrodes coupled to an unregulated current path is an anode.

\* \* \* \* \*